(12) United States Patent
Janicki et al.

(10) Patent No.: US 12,365,864 B1
(45) Date of Patent: Jul. 22, 2025

(54) SYSTEMS AND METHODS FOR PRODUCING AMMONIUM NITRATE

(71) Applicant: Sedron Technologies, LLC, Sedro Woolley, WA (US)

(72) Inventors: Stanley Janicki, Mount Vernon, WA (US); Peter William Janicki, Mount Vernon, WA (US); Liam Joseph Potocsnak, Lake Stevens, WA (US)

(73) Assignee: Sedron Technologies, LLC, Sedro Woolley, WA (US)

( * ) Notice: Subject to any disclaimer, the term of this patent is extended or adjusted under 35 U.S.C. 154(b) by 0 days.

(21) Appl. No.: 19/025,921

(22) Filed: Jan. 16, 2025

Related U.S. Application Data

(60) Provisional application No. 63/622,218, filed on Jan. 18, 2024.

(51) Int. Cl.
*C12M 1/36* (2006.01)
*C12M 1/00* (2006.01)
(Continued)

(52) U.S. Cl.
CPC ............ *C12M 41/48* (2013.01); *C12M 29/04* (2013.01); *C12M 29/18* (2013.01); *C12M 41/18* (2013.01);
(Continued)

(58) Field of Classification Search
CPC ...... C12M 41/48; C12M 41/18; C12M 41/26; C12M 41/32; C12M 41/34; C12M 41/36; C12M 29/04; C12M 29/18
(Continued)

(56) References Cited

U.S. PATENT DOCUMENTS 6,596,521 B1 * 7/2003 Chang .................... C12M 41/26
435/142
11,858,839 B2   1/2024 Giraldo et al.
(Continued)

FOREIGN PATENT DOCUMENTS

| WO | 2013133703 | 9/2013 |
| WO | 2014172121 | 10/2014 |
| WO | 2018100069 | 6/2018 |

OTHER PUBLICATIONS

Udert et al., "Complete nutrient recovery from source-separated urine by nitrification and distillation," Elsevier, Water Research 46, 2012, 12 pages.
(Continued)

*Primary Examiner* — Michael L Hobbs
(74) *Attorney, Agent, or Firm* — Perkins Coie LLP

(57) ABSTRACT

Systems and methods for producing ammonium nitrate are disclosed herein. Exemplary systems can comprise a bioreactor positioned to receive a feed including ammonia. The bioreactor can hold a liquid solution including (i) an ammonia oxidizing bacteria (AOB) and (ii) a nitrite oxidizing bacteria (NOB). The AOB can facilitate oxidation of the ammonia to produce a nitrite at a nitritation rate and the NOB can facilitate oxidation of the nitrite at a nitratation rate. Thus, the bioreactor can produce a mixed liquor comprising a nitrate biologically. The system can further comprise a filter positioned to receive the mixed liquor and produce a permeate and a sludge. A sensor can measure the concentration of the liquid solution of the bioreactor, and a controller coupled to the sensor can regulate the mass flow of nitrogen and/or phosphorus of the bioreactor feed based on the measured concentration of the liquid solution.

30 Claims, 4 Drawing Sheets

(51) Int. Cl.
*C12M 1/02* (2006.01)
*C12M 1/34* (2006.01)

(52) U.S. Cl.
CPC ............ *C12M 41/26* (2013.01); *C12M 41/32* (2013.01); *C12M 41/34* (2013.01); *C12M 41/36* (2013.01)

(58) Field of Classification Search
USPC ..................................................... 435/283.1
See application file for complete search history.

(56) References Cited

U.S. PATENT DOCUMENTS

| | | |
|---|---|---|
| 11,919,827 B2 | 3/2024 | Giraldo et al. |
| 2009/0301963 A1* | 12/2009 | Brockmann ........... B01D 61/18 210/601 |
| 2013/0001160 A1 | 1/2013 | Nyhuis et al. |
| 2013/0115588 A1* | 5/2013 | Davis ..................... C12M 33/14 435/286.1 |
| 2024/0083791 A1 | 3/2024 | Giraldo et al. |
| 2024/0083792 A1 | 3/2024 | Giraldo et al. |

OTHER PUBLICATIONS

International Search Report and Written Opinion for International Patent Application No. PCT/US2025/011917, Applicant: Sedron Technologies, LLC, mailed May 13, 2025, 10 pages.

* cited by examiner

SYSTEMS AND METHODS FOR PRODUCING AMMONIUM NITRATE

CROSS-REFERENCE TO RELATED APPLICATIONS

The present application claims the benefit of U.S. Provisional Patent Application No. 63/622,218, filed Jan. 18, 2024, and titled "SYSTEMS AND METHODS FOR PRODUCING AMMONIUM NITRATE," the disclosure of which is incorporated herein by reference in its entirety.

TECHNICAL FIELD

This disclosure relates to systems and methods for producing ammonium nitrate. In particular embodiments, this disclosure relates to an industrial system for producing ammonium nitrate using a partial nitritation process and/or a complete nitratation process.

BACKGROUND

Nitrogen recovery lies at the intersection of two industries: wastewater treatment and agriculture. The wastewater treatment industry has historically leveraged biological treatment to remove nitrogen, most commonly in the form of ammonia, prior to returning treated water to the environment. Commonly used methods for treating wastewater include nitrification and denitrification, as well as an anammox process. Nitrification and denitrification involve a sequential two-step process with ammonia-oxidizing bacteria (AOB), nitrite-oxidizing bacteria (NOB), and denitrifying bacteria, while the anammox process involves anaerobic ammonium-oxidizing bacteria that convert ammonia and nitrite directly into nitrogen gas. However, these processes are energy-intensive, typically requiring significant aeration and chemical additives for pH buffering and supporting heterotrophic biomass and may also necessitate pH adjustment and additional carbon sources, further increasing operational costs.

In the agricultural industry, nitrogen in wastewater is considered a valuable nutrient with significant incentives to reuse and recover, for example, as a fertilizer. However, the volatility of ammonia and the inefficiency of traditional nitrogen recovery methods limit the effectiveness of nitrogen recovery. Furthermore, the volatility of ammonia results in significant nitrogen loss during storage and land application, leading to odorous emissions and inefficient nutrient recovery. Additionally, the nutrient composition of recovered nitrogen may not be ideal for soil amendment, and its dilute nature limits its application to local areas. These limitations highlight the need for alternative systems and methods that can produce ammonium nitrate without the drawbacks associated with current techniques, providing a more efficient and economical approach to nitrogen recovery that benefits both the wastewater treatment and agricultural industries.

BRIEF DESCRIPTION OF THE DRAWINGS

Features, aspects, and advantages of the presently disclosed technology may be better understood with regard to the following drawings.

Figure 1:
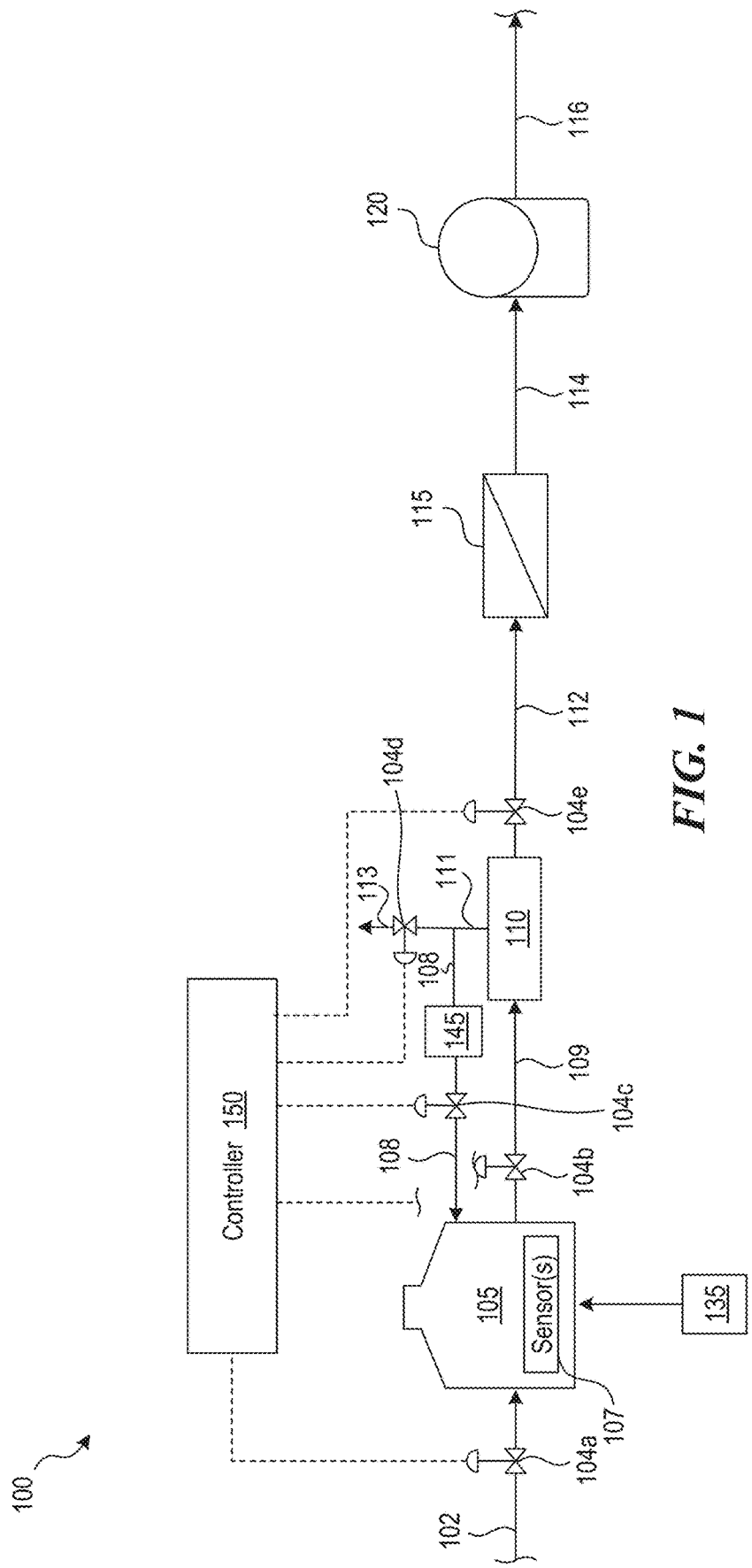
FIG. 1 illustrates a schematic view of an industrial system for producing ammonium nitrate, in accordance with embodiments of the present technology.

A person skilled in the relevant art will understand that the features shown in the drawings are for purposes of illustrations, and variations, including different and/or additional features and arrangements thereof, are possible.

DETAILED DESCRIPTION

I. Overview

The present technology is generally directed to producing ammonium nitrate using an industrial system. Nitrogen recovery lies at the intersection of two industries: wastewater treatment and agriculture. The wastewater treatment industry has historically leveraged biological treatment to remove nitrogen, most commonly in the form of ammonia, prior to returning treated water to the environment. Consequences of releasing untreated high-strength ammonia wastewater are numerous and severe, which has motivated the development of biological nutrient removal (BNR) technology that is robust and efficient. The most common method used is a sequential two-step process including nitrification and denitrification.

In nitrification, ammonia oxidizing bacteria (AOB) (e.g., *Nitrosococcus, Nitrosospira, Nitrosomonas*, etc.) oxidize ammonia to nitrite through the process of nitritation, and nitrite oxidizing bacteria (NOB) (e.g., *Nitrospira, Nitrococcus, Nitrospina, Nitrobacter*, etc.) then oxidize nitrite to nitrate through the process of nitratation in an aerobic bioreactor. Nitrification is also referred to as the conversion of ammonia (a weak base) to nitric acid (e.g., a strong acid). The nitritation reaction is typically rate limiting and produces a proton (e.g., the strong acid) during the complete nitrification process. As a result, pH decreases and chemicals (e.g., sodium hydroxide) are often added to control pH within a desired range. For example, common pH adjusters include a salt of bicarbonate or carbonate, which has buffer capacity near the optimal pH range for nitrifying bacteria. However, by adding such chemicals and increasing alkalinity, obtaining certified organic classifications of the resulting product becomes more difficult. The production of ammonium nitrate using the nitrification process can be a part of a Water Waste Treatment Plant (WWTP). However, current WWTPs utilize the nitrification process for goals that differ from producing ammonium nitrate (e.g., denitrification, chemical oxygen demand (COD) removal, biochemical oxygen demand (BOD) removal, phosphorus removal, etc.). Common incompatibilities of using the nitrification process include the requirement of large alkalinity addition to prevent pH crashes during the nitritation reaction.

Denitrification is the oxidation of organic carbon with oxygen from the reduction of nitrite and nitrate and cannot occur without organic carbon to oxidize. Wastewater with insufficient organic carbon, or a low carbon to nitrogen (C:N) ratio, requires dosing via a carbon source to remove all nitrogen via denitrification. In denitrification, facultative heterotrophic bacteria reduce nitrate to nitrogen gas to oxidize organic carbon in an anaerobic bioreactor. The result is nitrogen removal to the atmosphere. AOB and NOB, as discussed above, are both chemolithoautotrophs and obligate aerobes, which require oxygen to grow. This contrasts with facultative aerobes that, like the heterotrophic bacteria used in denitrification, prefer oxygen as an electron donor, but may use other compounds (such as nitrite or nitrate in the case of denitrification) in a less energetically favorable mechanism when in anoxic conditions. This process is effective for nitrogen recovery, but energy-intensive, with the primary cost being aeration during the nitrification stage. The process may also require additives for pH buffering and for supporting the heterotrophic biomass.

Ammonium nitrate can also be produced using partial nitritation facilitated by anaerobic ammonium oxidation, often referred to as anammox. In the 1990s, annamox was discovered to improve on conventional denitrification for high-strength ammonia wastewater with low C:N ratios. Anammox is an enzyme-catalyzed reaction of ammonia and nitrite in anaerobic conditions to yield nitrogen gas and water. Anammox often follows partial nitritation in a process called Partial Nitrification-Anammox (PNA). Partial nitritation is the process in which AOB oxidize a fraction of the ammonia to nitrite while NOB are ideally eliminated to prevent oxidation of nitrite to nitrate. This results in an ammonium nitrite stream suitable for treatment by anammox. This process reduces aeration load significantly by removing all nitrite oxidation and approximately half of the ammonia oxidation. PNA does not require pH adjustment, as partial nitritation leaves basic ammonia in the solution to balance the acidic nitrite. Anammox also does not require organic carbon to achieve nitrogen removal, meaning that wastewater with low C:N ratios can be treated without additional organic carbon. Anammox currently stands as the most efficient method of biological nitrogen removal for high-strength ammonia wastewater with a low C:N ratio, though it remains sparsely implemented in industry largely as a result of the inherently long timescale of startup for the bacteria and the complexity (compared to denitrification) of the process controls required for robust operation. These systems can also be used to circumvent oxygen requirements for nitratation to achieve nitrogen removal. Additionally, such systems produce a generally large number of nitrites or nitrite nitrogen (NO2-N) that are volatile/degradable and inhibit NOB activity. In some cases, the inhibition of NOB activity eliminates NOB from such systems entirely. As a result, such systems limit the amount of ammonium nitrate that can be produced at an industrial scale.

In contrast to wastewater treatment, agriculture has historically treated nitrogen in wastewater as a nutrient to be recovered. Nutrients are a requirement for the growth of crops and livestock, and as such there is tremendous incentive to recover and reuse nutrients present in the wastewater of an agricultural process. For example, it is common for the manure at a dairy farm to be reapplied to fertilize the crops which in turn feed the cattle. This process is limited in its effectiveness for a number of reasons. One inefficiency particular to nitrogen recovery is the volatility of ammonia. Before manure is applied, significant loss to volatilizing can occur in lagoon storage. When land-applied, the ammonia content of the manure again volatilizes to a high degree, resulting in odorous emissions and inefficient nitrogen recovery if the manure is not rapidly incorporated. The manure also contains other nutrients like phosphorus and potassium in a ratio that may not be desirable for soil amendment. The manure can be challenging to pump and spray, it is corrosive to equipment, and is too dilute to be efficiently applied anywhere other than locally, limiting its effectiveness. For example, most of the crops consumed by livestock are not grown locally, and the recovered nutrients most needed are to replace the nutrients in the soil where the feed crops were grown.

Embodiments of the present technology address at least some of the above-described issues in treating wastewater and nutrient recovery processes. Such embodiments can include an industrial system that utilizes a mechanical vapor recompression cycle for processing wastewater and separating suspended and dissolved solids from water and dissolved volatiles. When applied to manure, the industrial system can produce a dewatered solid product containing potassium, phosphorus, and organic nitrogen (dry product) and a distilled liquid containing dissolved ammonia and volatile organic compounds (condensate). Dewatering achieves significant volume reduction of the solids and reduces the cost to ship and apply the nutrients. The liquid product can also be easily pumped, and can isolate nitrogen as a nutrient for targeted soil amendment while remaining dilute.

Embodiments of the present technology can be further directed towards a partial nitritation and complete nitratation process (referred to herein as a "partial nitrification process") used to stabilize high strength ammonia wastewater. Partial nitrification requires partial (i.e., not complete) nitritation to convert a fraction (e.g., less than 50%, 60%, 70%, 80%, 90%, or 100%) of the ammonia to nitrite. Moreover, unlike PNA, partial nitrification relies on a comparatively higher rate of nitratation by NOB than nitritation by AOB to convert nearly all of the nitrite to nitrate. Nitrite is readily decomposed into nitrogen oxides, a process that is exacerbated with elevated temperature. This necessitates the conversion of ammonia to nitrate to prevent nitrogen loss, e.g., to decomposition. The result is a stable ammonium nitrate solution that requires no added buffers, no additional carbon to support heterotrophic biomass, and which has a neutral pH. The ammonium nitrate solution can then be concentrated by various means, including reverse osmosis (RO) and evaporation, to produce a stable, concentrated ammonium nitrate solution. Based on the cost evaluation of the product and the projected cost of a full-scale production plant, the industrial system disclosed herein affords economical nutrient recovery for dairy manure and other high-strength ammonia wastewaters not exclusive to agriculture.

Embodiments of the present technology can include systems having controls to create an environment that favors nitratation relative to nitritation and maintains desired pH levels. In some embodiments, the system is paired with mass transfer equipment configured to strip the ammonia from the liquid and concentrate it in a vapor stream, which can be condensed to produce a concentrated aqueous ammonia product (e.g., the aqueous ammonia liquid product). This product is valuable as a nitrogen fertilizer, but can be volatile, thus effecting the product's separation and concentration. The system of the present technology can include a cost-effective method for stabilizing the nitrogen to create a higher-value fertilizer product. As explained herein, the industrial system can also produce a concentrated product of ammonium nitrate (e.g., having approximately a one-to-one ratio of ammoniacal nitrogen (e.g., free ammonia and ammonium) to nitrate nitrogen) with no or limited residual nitrite. The resulting concentrated product can qualitatively have a distinct odor, though it is not offensive or strong in comparison to the odor of ammonia as described above, despite being many-times greater in concentration. The concentrated product can be a dark caramel, transparent liquid with low turbidity that can be stored in shelf storage long-term with no settling, clarifying, or measurable decrease in product concentration. This in turn can confirm the concentrated product's overall greater stability to products of other nutrient recovery systems.

Since nitrogen in any form (e.g., ammonia, nitrate, nitrite, etc.) can have negative impacts on the environment, nitrogen is removed from traditional wastewater treatment. Nitrification/Denitrification, and Partial Nitrification-Anammox (PNA) processes aim to remove nitrogen from wastewater in processes that minimize the environmental impact of nitrogen. However, the resulting products of these processes (e.g., ammonia, nitrogen gas, nitrate, excess biomass, etc.) are typically not used in a closed loop mechanism, meaning the resulting products are not typically recovered as nutrients. There is also a cost factor associated with nutrient recovery to produce ammonium nitrate. For example, chemical compounds (e.g., nitric acid) can be mixed with recovered ammonia at a lower cost than using equipment to purify the recovered nutrients through certified organic processes. Thus, the combination of wastewater treatment and nutrient recovery to produce a concentrated ammonia nitrate product that is certified organic would not be obvious to one of ordinary skill in the art.

Additionally, the reactions that facilitate common wastewater treatment processes are often done in completion (e.g., complete nitrification). If a bioreactor is used for complete nitrification, all excess ammonia in the bioreactor is consumed. The use of the partial nitrification process allows for the active bacteria in the bioreactor to grow and stabilize, since ammonia is not consumed as rapidly. For example, when maintaining partial ammonia oxidation, any substance that grows slower than AOB will be washed away from the bioreactor and any substance that grows fasters than AOB (e.g., NOB and heterotrophic organisms) will stabilize once something limits its growth (e.g., substrate-limited conditions). Additionally, the nutrients recovered throughout the system, as described herein, can be reintroduced to the bioreactor to facilitate growth and stability of the active bacteria.

In addition to using a partial nitrification process, embodiments of the present technology can include multi-component systems to produce ammonium nitrate. For example, embodiments of the present technology can comprise a system that includes a bioreactor, a filter, a sensor, and a controller. The bioreactor can be positioned to receive a feed containing ammonia, phosphorous, and/or carbon, and can hold a liquid solution including a biologically active (e.g., living) population of bacteria (e.g., AOB and NOB). The AOB can facilitate oxidation of the ammonia to produce a nitrite at a nitritation rate, and the NOB can facilitate oxidation of the nitrite at a nitratation rate. In doing so, the bioreactor can produce a mixed liquor comprising nitrate. The system further comprises a filter positioned to (i) receive the mixed liquor and (ii) produce a permeate and a sludge. Sensors can be used to measure the pH, concentrations (e.g., oxygen levels), and/or temperature of the liquid solution of the bioreactor.

In biological systems, there are diverse trace micronutrients that can optimize the functioning of the system, such as orthophosphate phosphorus. If a typical manure waste stream is used to add these micronutrients, phosphorus is generally the limiting micronutrient. In such cases, regulating the mass flow of phosphorus, for example via a phosphorus-containing micronutrient solution, to achieve a target phosphorus loading can optimize the stability of the biological system. A controller coupled to the sensors can regulate the mass flow of nitrogen and/or phosphorus of the feed to the bioreactor based on the measured pH, concentrations, and/or temperature of the liquid solution. In some embodiments, the change in the mass flow of nitrogen and/or phosphorus results in a new mass flow of nitrogen and/or phosphorus that differs from the one required by the system to process ammonia upstream (e.g., discrepancies in the amount of amount ammonia stored versus absorbed). Sludge wasting can be used to account for the change in mass flow of nitrogen and/or phosphorus. For example, sludge wasting can regulate the AOB population in the bioreactor which, in turn, regulates the ammonia oxidation rate. This, in turn, allows the system to maintain pH without affecting the mass flow of nitrogen and/or phosphorus needed upstream.

It is worth noting that the distinction between partial nitrification and partial nitritation, as both are commonly abbreviated PN and are sometimes used interchangeably when describing the process whereby ammonia is partially oxidized to nitrite prior to nitrogen removal by anammox. The processes of partial nitrification and partial nitritation are distinct processes and are treated as such herein. Partial nitrification, as used herein, is defined as the partial oxidation of ammonia to nitrite (partial nitritation) and the complete oxidation of the resulting nitrite to nitrate (complete nitratation), amounting to nitrification on a part of the available ammonia. As defined as such, partial nitrification has not been successfully implemented at an industrial scale.

In the Figures, identical reference numbers identify generally similar, and/or identical, elements. Many of the details, dimensions, and other features shown in the Figures are merely illustrative of particular embodiments of the disclosed technology. Accordingly, other embodiments can have other details, dimensions, and features without departing from the spirit or scope of the disclosure. In addition, those of ordinary skill in the art will appreciate that further embodiments of the various disclosed technologies can be practiced without several of the details described below.

II. Systems and Methods for Producing Ammonium Nitrate

FIG. 1 is a schematic view of an industrial system 100 for producing a concentrated product 116 (e.g., ammonium nitrate), in accordance with embodiments of the present technology. The industrial system 100 can include a bioreactor 105, a filter 110 downstream of or disposed within the bioreactor 105, a reverse osmosis (RO) unit 115 downstream of the filter 110, and an evaporator 120 downstream of the RO unit 115. The industrial system 100 further includes one or more valves 104a-e (collectively referred to as "valves 104") each configured to regulate fluid flow within the industrial system 100, one or more sensor(s) 107 (referred to as "sensor(s) 107"), and a controller 150 in communication with the valves 104 and the sensor(s) 107. In some embodiments, the valves 104 are pumps or another controlling mechanism for regulating the fluid flow within the industrial system 100. In addition, the industrial system 100 can include a feed 102 comprising ammonia and/or ammonium, a mixed liquor 109 exiting the bioreactor 105, a sludge 111 exiting the filter 110, a return sludge 108 comprising a portion of the sludge 111 directed to the bioreactor 105, a waste sludge 113 comprising a portion of the sludge 111 directed to waste, a permeate 112 exiting the filter 110 and directed toward the RO unit 115, a retentate 114 exiting the RO unit 115 and directed toward the evaporator 120, and the concentrated product 116 exiting the evaporator 120.

As shown in FIG. 1, the feed 102 is fed into the bioreactor 105. The bioreactor 105 can house a liquid solution that comprises the ammonia/ammonium from the feed 102, along with AOB and NOB. The feed 102 can further comprise phosphorous, carbon, and/or unprocessed manure. The unprocessed manure can contain small quantities of trace micronutrients. For example, the micronutrients are elements, such as calcium and magnesium, that facilitate activity and/or growth of AOB and NOB. The ammonia/ammonium in the feed 102 is typically distilled ammonia/ammonium, and therefore, lacks micronutrients. The unprocessed manure can be used to reintroduce micronutrients back into the bioreactor 105 that the feed 102 otherwise would be missing. The AOB can facilitate oxidation of the ammonia in the feed 102 to produce a nitrite at a nitritation rate, and the NOB can facilitate oxidation of the nitrite at a nitratation rate to produce nitrate. The mixed liquor 109 provided by the bioreactor 105 comprises nitrate and is received by the filter 110. Without being bound by theory, the ammonia and ammonium of the feed 102 can act as a buffer to maintain the desired pH of the liquid solution in the bioreactor 105, and the phosphorus of the feed 102 can facilitate the activity and/or growth of the AOB and NOB.

The bioreactor 105 contains a biologically active population of bacteria (e.g., AOB and NOB). The use of AOB and NOB in the bioreactor 105 facilitates production of nitrate biologically (e.g., without the addition of chemicals). The activity of the bacteria in the liquid solution can change and/or be optimized based on the composition of the feed 102. For example, the composition of a carbon to nitrogen to phosphorus (C:N:P) ratio, or a ratio of units of mass of biochemical oxygen demand to ammonia nitrogen to phosphate phosphorus (BOD:NH3-N:PO4-P) can effect nitrogen recovery, and thus, partial nitrification. The typical ratio of carbon to nitrogen to phosphorus (C:N:P) in most WWTP systems is approximately 100:5:1. This means in most WWTP systems, to oxidize organic carbon, the active population of bacteria assimilates nitrogen from ammonia and phosphorous from orthophosphate in the feed 102 at a ratio of approximately 100:5:1. If any less nitrogen or phosphorus is available to be assimilated, then not all of the BOD may be oxidized due to nutrient-limiting conditions. Additionally, at this ratio, no nitrification occurs, because all the nitrogen available is assimilated by the active population of bacteria. Thus, this ratio does not favor nitrogen recovery and, moreover, can reduce the active population of bacteria in the bioreactor 105 by reducing the oxygen and/or energy available in the industrial system 100.

Organic carbon can result in an increase in the heterotrophic bacteria population in the bioreactor which, in turn, can produce byproducts of cellular metabolism that foul concentration equipment (e.g., the RO unit 115 and the evaporator 120) downstream from the bioreactor 105 in the industrial system 100. Thus, in some embodiments, the feed 102 does not include organic carbon. For example, in typical WWTP systems that want to oxidize all of the ammonia present (e.g., complete nitrification), the feed 102 maintains a ratio of nitrogen to phosphorous (N:P) that is at least 150:1, 200:1, 225:1, 250:1, or 275:1, a range of 150:1-275:1, or any value therebetween. For example, to oxidize ammonia, the active population of bacteria assimilate nitrogen from ammonia and phosphorous from orthophosphate in the feed 102 at a ratio of 200:1. If any less phosphorus is included, not all of the ammonia may be oxidized due to nutrient-limiting conditions. Thus, to oxidize only half of the ammonia present (e.g., partial nitrification), the feed 102 can maintain a ratio of N:P that is at least 350:1, 375:1, 400:1, 425:1, 450:1, or 475:1, a range of 350:1-475:1, or any value therebetween, as described further herein.

In contrast to the typical ratios used in WWTP systems, the industrial system 100 can maintain the C:N:P ratio of the feed 102 at more desirable ratios (e.g., a C:N:P ratio of at most 10:310:1, 15:335:1, 20:360:1, 25:385:1, 30:410:1, or 35:435:1, a range of 10-35:285-435:1, or any value therebetween) that favors partial nitrification and maintains the desired composition and performance of the bacteria in the liquid solution. This C:N:P ratio loses no ammonia to heterotroph growth and has only as much phosphorus as is needed to support a 1:1 relationship between ammonia nitrified to residual ammonia. Therefore, the industrial system 100 can recover approximately all of the nitrogen (e.g., at least 98%) as ammonium nitrate. In some embodiments, the nitrogen lost in the industrial system 100 (e.g., the remaining 2%) supports growth of the active population of bacteria. The composition and performance of the active population of bacteria can be monitored by determining how efficiently nitrogen can be recovered by partial nitrification. In some embodiments, if the industrial system 100 has a lower hydraulic residence time (HRT), the biomass concentration would be higher. Additionally or alternatively, if the industrial system 100 has a higher HRT, the biomass concentration can be lower. In some embodiments, the HRT is at most 0.5 days, 1 day, 5 days, 10 days, or 20 days, a range of 0.5 to 20 days, or any value therebetween. The biomass concentrations can also vary with ammonia concentration in the feed 102, with more ammonia in the feed 102 requiring a greater biomass concentration to nitrify all of the ammonia. For example, in an industrial system 100 where the feed 102 has an ammonia concentration of 1800 parts per million (ppm) and an HRT of approximately one day, the amount of AOB in the liquid solution of the bioreactor is at most 400, 600, 800, 1600, or 3600 mg/L COD AOB, a range of 400-3600 mg/L COD AOB, or any value therebetween. COD AOB is defined as the measure of biomass concentration of AOB as COD, or the amount of oxygen it would take to oxidize the carbon in the organic compounds of the AOB cells. Additionally or alternatively, the ammonia nitrogen (NH3-N): COD AOB/day, or the ratio of the loading rate of ammonia nitrogen to the mass of biology for AOB, can be at most 0.5, 1, 2.5, 4.5, or 5 mg-N/mg-COD AOB/day, a range of 0.0.5 and 5 mg-N/mg-COD AOB/day, or any value therebetween. In some embodiments, for an industrial system 100 where the feed 102 has an ammonia concentration of 1800 ppm and an HRT of approximately one day, the amount of NOB in the liquid solution of the bioreactor is at most 100, 500, 1500, 3000, or 6000 mg/L COD NOB, a range of 400-6000 mg/L COD NOB, or any value therebetween. COD NOB is defined as the measure of biomass concentration of NOB as COD, or the amount of oxygen it would take to oxidize the carbon in the organic compounds of the NOB cells. Additionally or alternatively, the NO2-N: COD NOB/day, or the ratio of the loading rate of nitrite nitrogen to the mass of biology for NOB, can be at most 0.15, 0.6, 1.5, 3, or 9 mg-N/mg-COD NOB/day, a range of 0.15 and 9 mg-N/mg-COD NOB/day, or any value therebetween. In some embodiments, a food to microorganism ratio (F/M) for autotrophic and/or nitrifier biomass (e.g., AOB and NOB) is used to monitor composition and performance of the bioreactor 105, as described further herein.

In some embodiments, as long as the N:P ratio is at least 5:1, 6:1, 7.5:1, 10:1, 15:1, 20:1, or 25:1, a range of 5-25:1, or any value therebetween, the industrial system 100 can lose nitrogen and phosphorus according to the 5:1 ratio of a typical WWTP stream until any BOD present is oxidized.

Thus, the ratio of N:P in the feed 102 can be at least 5:1, 6:1, 7.5:1, 10:1, 15:1, 20:1, or 25:1, a range of 5-25:1, or any value therebetween. Once nutrient loss is account for, the feed stream 102 can be increased to a more desirable N:P ratio (e.g., 400:1). Thus, facilitating partial nitrification of any remaining ammonia.

Additionally or alternatively, and as explained herein, such ratios of the present technology can be enabled by regulating the AOB in the bioreactor, e.g., by removing a population of the active bacteria from the industrial system 100 at a rate that is faster than the rate that the active bacteria in the bioreactor 105 capture ammonia and convert ammonia to nitrite. In some embodiments, AOB is regulated to avoid over-oxidizing ammonia. This can be done by regulating the rate of waste sludge 113, and/or the rate of waste sludge 113 relative to the rate of return sludge 108. Wasting can be used to maintain an AOB population that oxidizes the required fraction of the ammonia being fed to the bioreactor 105. The AOB population, in turn, can impact the growth rate of heterotrophs and NOB in the bioreactor 105.

The bioreactor 105 can be or can include a membrane bioreactor (MBR), an activated sludge bioreactor, or other bioreactor that contains an aerated tank and a filtration system to remove liquid or soluble constituents and retain insoluble mass from the mixed liquor 109. The bioreactor 105 can contain the active population of bacteria (e.g., AOB and NOB) as an activated sludge that mixes with the feed 102 and the return sludge 108 to produce the mixed liquor 109. The aerated tank can be used to regulate the environment (e.g., temperature and DO) of the bioreactor 105 for the active population of bacteria. In addition, nutrients from the feed 102 (e.g., soluble biodegradable organics) can allow the active bacteria in the bioreactor 105 to make energy and grow. For example, the feed 102 can contain unprocessed manure (e.g., carbon and phosphorus) that the AOB and NOB use to make energy, grow, and treat the contents of the bioreactor 105 (e.g., via the partial nitrification process). The filtration system allows liquid to be removed from the industrial system 100 without unnecessarily removing biomass (e.g., the activated sludge). Conventional activated sludge systems use gravity clarifiers for this purpose and recollect a fraction of the sludge in a return line from the settled bottoms of the clarifier. However, gravity clarifiers can take up a large amount of space and lead to variable results depending on the settling properties of the mixed liquor (e.g., greater biomass loss than is desirable if settleability is poor or flowrate is too high). The bioreactor 105 facilitates improved control of filtration with a smaller footprint by implementing a filtration system that separates liquid and soluble constituents from solids (e.g., biomass). The filtration system is discussed in more detail to with reference to the filter 110 of FIG. 1.

It is worth noting that the bioreactor 105 is not limited to the MBR or the activated sludge bioreactor system. For example, the bioreactor 105 can be or can include a membrane-aerated biofilm reactor (MABR) that contains an aeration system which allows for low energy delivery of oxygen into the bioreactor, reducing the amount of dissolved oxygen added to the bioreactor. Additionally or alternatively, the bioreactor 105, can be split into multiple bioreactors. For example, a first bioreactor can contain AOB to facilitate oxidation of the ammonia to produce a nitrite at a nitritation rate, and a second bioreactor, downstream of and fluidically coupled to the first bioreactor, can contain NOB to facilitate oxidation of the nitrite produced in the first bioreactor at a nitratation rate.

As further shown in FIG. 1, the bioreactor 105 can include the sensor(s) 107. The sensor(s) 107 can be used and/or configured to measure a concentration of the liquid solution within the bioreactor 105, and can include a pH sensor, an ammonia sensor, an ammonium sensor, a nitrate sensor, and/or a nitrite sensor. In some embodiments, the pH and/or the concentration (e.g., of ammonia, ammonium, nitrite, nitrate, phosphorous, phosphate, etc.) measured via the sensor(s) 107 causes the controller 150 to regulate the mass flow of nitrogen and/or phosphorous of the feed 102 to the bioreactor 105.

In some embodiments, phosphorus is a limiting nutrient in the bioreactor 105. Additionally or alternatively, the feed 102 can comprise a carbon:phosphorus (C:P) ratio of at most 90:1, 95:1, 100:1, 105:1, 110:1, or 115:1, a range of 90-115:1, or any value therebetween to support BOD oxidation, and/or a nitrogen:phosphorus (N:P) ratio of at least 5:1, 6:1, 7.5:1, 10:1, 15:1, 20:1, or 25:1, a range of 5-25:1, or any value therebetween. Carbon and nitrogen both consume phosphorous in the bioreactor; therefore, phosphorous can limit the oxidation of carbon and ammonia/nitrite if it is the limiting nutrient in the bioreactor 105. If phosphorus is the limiting nutrient, the pH in the bioreactor will be high because AOB will be unable to oxidize enough ammonia to drop the pH and stabilize the remaining ammonia. Thus, it is ideal for the bioreactor 105 to maintain nutrient levels that stabilize the activity and/or growth of the active bacteria to maintain a partial nitrification environment. Additionally or alternatively, the activity and/or growth of the active bacteria, if phosphorus is not a limiting nutrient, can be proportional to the C:N ratio of the feed 102 or the amount of ammonia and nitrite in the system. For example, the C:N ratio can be representative of nitrogen loss by determining nitrogen lost to bacteria growth and carbon oxidized.

It can be advantageous to monitor the phosphate and/or phosphorus concentration in the bioreactor 105 to gain insights into the overall performance of the bioreactor 105 and to adjust the concentration of the feed 102 (e.g., by causing the controller 150 to regulate the mass flow of nitrogen and/or phosphorus of the feed 102). As discussed herein, phosphorous can enable microbial growth and metabolic activities within the bioreactor 105. More specifically, phosphate is a key component of ATP, nucleic acids, and phospholipids, which are indicative of energy transfer, genetic information, and cell membrane integrity. Insufficient levels of phosphate can lead to suboptimal performance and reduced efficiency of the bioreactor 105 and the overall system 100. In some embodiments, the phosphate concentration in the bioreactor 105 is at least 0.1, 0.3, 0.5, 0.7, or 1.0 ppm, a range of 0.1 and 1.0 ppm, or any value therebetween to ensure optimal performance and efficiency of the bioreactor 105 by maintaining generally higher biomass production. The controller 150 can be configured to monitor phosphate levels in the bioreactor via the sensor(s) 107. For example, if the phosphate concentration in the bioreactor 105 drop below 0.3 ppm, the controller 150 can adjust the concentration of the feed 102 such that mass flow of phosphorous of the feed 102 restores the levels of phosphate to at least 0.3 ppm.

The controller 150 can be configured to regulate pH levels, oxygen levels, and/or the temperature of the liquid solution in the bioreactor 105. More specifically, the controller 150 can regulate pH, DO, and temperature. Moreover, by controlling one or more of these variables, the controller 150 can regulate an amount of bacteria by monitoring the activity and/or growth rate of the bacteria within the bioreactor 105. In some embodiments, pH, DO, and temperature are determinants for monitoring partial nitrification.

The controller 150 can be configured to regulate the concentration of the liquid solution of the bioreactor 105 by opening or closing the valves 104. More specifically, the controller 150 can regulate feed rate (e.g., by adjusting valve 104a), production rate (e.g., by adjusting valve 104b), recycle rate (e.g., by adjusting valve 104c), waste rate (e.g., by adjusting valve 104d), and permeate rate (e.g., by adjusting valve 104e). For example, the controller 150 can regulate the mass flow of nitrogen and/or phosphorous of the feed 102 containing ammonia to the bioreactor 105 by opening or closing the valve 104a. As described herein, the controller 150 can open or close the valves 104 based on the pH, concentrations, and/or temperature of the liquid solution of the bioreactor 105. For example, the controller 150 can be configured to regulate the mass flow of nitrogen and/or phosphorous of the feed 102 containing ammonia to the bioreactor 105 based on the measured pH by the sensor(s) 107 to maintain the pH of the liquid solution to be at most 6.5, 6.6, 6.7, 6.8, 6.9, or 7.0, a range of 6.5-7.0, or any value therebetween. Additionally or alternatively, the controller 150 can be configured to regulate the mass flow of nitrogen and/or phosphorous of the feed 102 containing ammonia to the bioreactor 105 based on the measured pH by sensor(s) 107 to maintain the pH of the liquid solution at a pH of at most 4.0, 4.5, 5.0, 5.5, 6.0, 6.5, or 7.0, a range of 4.0-7.0, or any value therebetween.

In some embodiments, the pH of the bioreactor 105 is regulated using the mass flow rate of the feed 102, the return sludge 108, and/or the waste sludge 113, as described herein. The mass flow rate of the waste sludge 113 can control the F/M ratio for autotrophic and/or nitrifier biomass. The F/M ratio can represent the rate food entering a biological system available to the autotrophic biomass population, e.g., the ratio of carbonaceous BOD to heterotrophic biomass. The F/M ratio can be measured in units of food per mass of the biomass per unit time. In addition, the F/M ratio is representative of the environment of the bioreactor 105 since the ratio is affected by the volume of the bioreactor 105, concentrations and/or flow rates of the feed 102, concentrations of biomass in the bioreactor 105 (e.g., AOB and NOB), and HRT. Thus, the F/M ratio can be used to monitor and maintain an environment that favors partial nitrification in the bioreactor 105. The nitrifier biomass can represent the food (e.g., ammoniacal nitrogen) entering a biological system available to the nitrifier biomass population (e.g., AOB or NOB). In an industrial system 100 that favors partial nitrification, the F/M ratio of AOB can be at least 0.5, 1, 1.5, 2.1, or 2.3 (lbs of ammonia oxidized/lbs AOB as COD)/day, a range of 0.5-2.3 (lbs of ammonia oxidized/lbs AOB as COD)/day, or any value therebetween. In an industrial system 100 that favors partial nitrification, the F/M ratio of NOB can be at least 0.3, 1.8, 3.6, 6.8, or 9 (lbs of nitrite oxidized/lbs NOB as COD)/day, a range of 0.3-9 (lbs of nitrite oxidized/lbs NOB as COD)/day, or any value therebetween. In some embodiments, pH control is achieved by setting infeed flow rates to the desired ratios (e.g., mass flow setpoints described herein), and the controller 150 is used to adjust the mass flow rates to maintain a near neutral pH.

In some embodiments, a blower 135 is positioned to introduce air into the bioreactor 105 and mix the liquid solution. The blower 135 can be used in conjunction with the sensor(s) 107. More specifically, the sensor(s) 107 can include an oxygen sensor positioned to measure oxygen and/or DO in the bioreactor 105. The controller 150 can be operably coupled to the blower 135 and the sensor(s) 107 to adjust the operation of the blower 135 based in part on the measured oxygen. For example, if the sensor(s) 107 detect too little DO, meaning there is a risk of inhibited nitratation, which could lead to nitrite accumulation in the bioreactor 105, the blower 135 can introduce more air into the bioreactor 105. In some embodiments, more than one blower is used to introduce air into the bioreactor 105. For example, two blowers can be positioned to introduce air into the bioreactor 105, e.g., at a minimum of one part per million or between one to four parts per million. Potential aeration methods can include a jet aeration system and a diffusion aeration system. The jet aeration system can include a recirculation loop of the liquid solution from the bioreactor 105 that is pumped through jets, and in turn, mixes the liquid solution with air (e.g., using the Venturi effect). This results in a mixed liquid solution that is reintroduced into the bioreactor 105 with more DO. The diffusion aeration system can include the blower 135 to pump air into a grid of diffusers, allowing air to form bubbles and rise through the bioreactor 105 into the liquid solution. Both aeration methods can introduce bubbles that diffuse oxygen into the liquid solution while also providing the agitation necessary to fully mix the contents of the bioreactor 105. In some embodiments, the jet aeration system provides a more efficient transfer of oxygen into the bioreactor 105 than the diffusion aeration system at a larger scale.

The setpoint for DO can be calculated by determining the air volumetric flow required in the bioreactor 105 to maintain partial nitrification, also referred to herein as the DO setpoint. The DO setpoint can be regulated using the aeration systems controlled by the controller 150, as described herein. More specifically, DO can be monitored using the sensor(s) 107 (e.g., a Hach LDO probe) in the bioreactor 105, and the controller 150 can regulate the aeration system if the DO setpoint is not met. In some embodiments, a slime layer develops on the sensor(s) 107, resulting in measurements biased toward low DO levels. It is worth noting that measurements biased toward low DO can lead to an increase of the speed setpoint of the blower 135, as more aeration is required to permeate the slime layer and reduce the apparent DO error (e.g., a setpoint above 3.8 cfm/sq. ft.). Such errors can be solved by manual cleaning, which results in the blower speed returning to the DO setpoint. Monitoring and detecting DO errors prevents disturbances that increase oxygen demand in the bioreactor 105. In an industrial application, the industrial system 100 can undergo a regular cleaning cycle, operators can be trained to identify DO error trends, and/or an automated detection system can be implemented (e.g., measuring oxygen uptake rates against model-predicted oxygen uptake rates).

In some embodiments, a heat exchanger 145 is positioned along the return line directing the return sludge 108 to the bioreactor 105. The heat exchanger 145 can be used in conjunction with the sensor(s) 107. More specifically, the sensor(s) 107 can include a temperature sensor positioned to measure the temperature of the liquid solution in the bioreactor 105. The controller 150 can be operably coupled to the heat exchanger 145 and the sensor(s) 107 to adjust the operation of the heat exchanger 145 based in part on the measured temperature. The controller 150 can be configured to regulate the heat exchanger 145. The heat exchanger 145 can be used to transfer heat from a heat source to the liquid solution in the bioreactor 105. In some embodiments, the bioreactor 105 is in environmental conditions where only cooling by the heat exchanger 145 is required to maintain a setpoint temperature (e.g., 35° F., 55° F., 70° F., 100° F., or 120° F., a range of 35° F.-120° F. or approximately 70° F.).

The flow rate of cooling water can be controlled via a modulating control valve actuated by the controller 150 to minimize temperature error in the bioreactor 105. In some embodiments, the thermal capacitance of the liquid solution in the bioreactor 105 provides a low system bandwidth, allowing for precise control in temperature and concentration fluctuations. In some embodiments, the bioreactor 105 gains energy via friction from the return sludge 108 being heated by the ultrafilter 110 (e.g., friction in the compression of air for oxygenation, and the exothermic reactions of carbon, ammonia, and nitrite oxidation). The heat exchanger 145 can be used to cool the bioreactor back to the setpoint temperature.

In some embodiments, fouling occurs on the heat exchanger 145 resulting in a reduction in effectiveness of the heat exchanger 145 and requiring a greater flowrate of cooling water to maintain the temperature setpoint. Fouling can be both biological (slime on the liquid solution side) and inorganic (rust or scale on the cooling water side). In an industrial application, the industrial system 100 can undergo a regular cleaning cycle, operators can be trained to identify temperature trends for fouling, and/or the heat exchanger 145 can include temperature and pressure sensors to detect fouling.

In some embodiments, the industrial system 100 includes an evaporative cooling tower and a water recirculation system to provide cooling water for temperature control and other applications. The water recirculation system can be prone to scaling as water is evaporated and salts are accumulated downstream. To prevent scaling, anti-scalant can be dosed into the recirculating stream to measure the stream's conductivity prior to reintroduction. If conductivity reaches concerning levels, the cooling water tank can be partially drained and refilled with a permeate (e.g., a low-TDS RO permeate).

The controller 150 can also regulate the wasting rate of the bacteria (e.g., waste sludge 113), nitrogen (or ammonia) in the feed 102, and hydraulic residence time. Flow rates of the bioreactor 105 can be monitored to maintain inflow and outflow parameters. At steady state operation, the mixed liquor 109 is pumped to the ultrafilter 110 allowing for the permeate 112 to enter the RO unit 115. The ultrafilter 110 can include a 3-position valve or other mechanism that directs flow of the permeate 112 to the RO unit 115, return sludge 108 back into the bioreactor 105, and directs waste sludge 113 out of the industrial system 100. If the bioreactor 105 volume levels get too low (e.g., the permeate 112 flow exceeds infeed flow), then the permeate 112 can be recycled back into the bioreactor 105 with the return sludge 108 until the level is recovered to the setpoint. It is worth noting that the waste sludge 113 can also reduce the levels of the bioreactor 105, but it is not returned to the bioreactor 105. The HRT in the bioreactor 105 can be calculated from the total volume divided by the total influent and/or effluent rate of the permeate 112 and/or the waste sludge 113 in the system. More specifically, the HRT indicates the volume of the bioreactor 105 and can be measured indirectly by monitoring relative flow rates of the feed 102, the mixed liquor 109, the return sludge 108, and/or the waste sludge 113. For example, the flow rate of the waste sludge 113 can be around 7% of the total influent and/or effluent flow rate of 400 gallons/minute for a 600,000-gallon bioreactor, or 28 gallons/minute, and thus, the bioreactor 105 refills itself everyday (e.g., a hydraulic residence time of one day). In some embodiments, the HRT is independent of the waste sludge 113 flow rate as long as the flow rates of the permeate 112 and/or the waste sludge 113 correspond to the flow rate of the feed 102, ensuring that the bioreactor 105 maintains a predetermined total volume. It is worth noting that "correspond to," when used in the context of the present disclosure, can mean+/− less than 20%, 15%, 10%, or 5% of the flow rate of the feed 102 (e.g., a mass flow of nitrogen and/or phosphorus of the feed 102 and/or a flow rate of one or more additional or alternative components of the system 100). In some embodiments, the HRT is directly related to a mixed liquor thickness (MLSS). Benefits of a higher MLSS include a lower wasting rate required to maintain the active population of bacteria. Drawbacks of a higher MLSS include a reduced oxygen mass transfer rate (e.g., requiring greater blower power to maintain DO setpoint) and/or reduced filterability (e.g., requiring a larger filter and/or more frequent cleaning of the filter).

The controller 150 can regulate the mass flow of nitrogen and/or phosphorous of the feed 102 to the bioreactor and (i) inhibit the rate of nitritation relative to the rate of nitratation and/or (ii) promote the rate of nitratation relative to the rate of nitritation. For example, if the sensor(s) 107 measured the concentration of nitrate to be low relative to the concentration of ammonia and the concentration of nitrite, the controller 150 can regulate the mass flow of nitrogen and/or phosphorous of the feed 102 to the bioreactor 105 to promote the rate of nitratation relative to the rate of nitritation. In some embodiments, the mass flow of nitrogen and/or phosphorous is regulated based on the measured concentrations from the sensor(s) 107 and whether a predetermined percentage (e.g., at most 40%, 45%, 50%, 55%, or 60%, a range of 40%-60%, or any value therebetween) of the ammonia in the liquid solution of the bioreactor 105 is oxidized and/or converted to nitrite to maintain pH to a pH setpoint. Additionally or alternatively, the percentage of ammonia oxidized in the liquid solution can be a consequence of the concentrations of all other buffers in the liquid solution. Similarly, the mass flow of nitrogen and/or phosphorous can be regulated based on the measured concentrations from the sensor(s) 107 and whether residual NO2-N (e.g., NO2-N that are unoxidized) remain in the liquid solution. For example, the residual NO2-N remaining in the liquid solution are at most 0.1, 1, 10, 25, or 50 ppm nitrite nitrogen. In some embodiments, there are no NO2-N remains in the liquid solution of the bioreactor (e.g., all of the NO2-N in the bioreactor are oxidized and/or converted). The amount of nitrite oxidized and/or converted will be based on the relative inhibition of AOB to NOB, which can be controlled by the pH of the bioreactor 105. NOB can consume nitrite until inhibition from nitrite shortage leads to a maintenance growth rate (e.g., the AOB and NOB growth rates correspond to the AOB and NOB wasting rates, respectively) resulting in stability for both populations of bacteria. Additionally or alternatively, the sensor(s) 107 can be used to maintain the alkalinity of the liquid solution of the bioreactor 105. More specifically, the alkalinity can be defined as a mass of alkalinity of calcium carbonate/mass of nitrified nitrogen. The alkalinity of the influent to support partial nitrification can be defined to be at most 0.5, 1, 2, or 3.6 lbs alkalinity/lb of nitrogen, a range of 0.5-3.6 lbs alkalinity/lb of nitrogen, or any value therebetween (e.g., well below the typical 7.41 lbs alkalinity (as CaCO3)/lb Nitrogen in the influent needed to support complete nitrification).

As described herein, the controller 150 can regulate the mass flow streams into different components of the industrial system 100 using the valves 104. For example, the controller 150 can be used to regulate the flow of the permeate 112 from the filter 110 to the RO unit 115 by opening or closing the valves 104. In some embodiments, the industrial system 100 is partially manually operated. For example, pH concentrations can be regulated using manual dosing of additives for pH control in the bioreactor. In some preferred embodiments, the industrial system 100 is partially or fully automated, e.g., by monitoring pH of the liquid solution of the bioreactor with sensors.

The filter 110 can be located downstream from the bioreactor 105 and positioned to receive the mixed liquor 109 and output the sludge 111 and the permeate 112. The mixed liquor 109 contains fluid that exists inside the bioreactor 105, including active bacteria from the bioreactor 105, components of the feed 102, and any products of the reactions within the bioreactor 105. For example, the mixed liquor 109 can contain ammonium, ammonia, and nitrate. In some embodiments, the mixed liquor 109 contains equal parts of nitrate nitrogen and ammoniacal nitrogen. For example, the mixed liquor 109 can include 1100 ppm of both the nitrate nitrogen and the ammoniacal nitrogen. Additionally, or alternatively, the mixed liquor 109 does not comprise NO2-N or comprises less than 50 ppm nitrite nitrogen.

The filter 110 can be an ultrafilter that the mixed liquor 109 passes through and can separate liquid and soluble constituents from solids or insoluble mass (e.g., biomass) in the mixed liquor 109. The filter 110 can come in different forms, such as a cassette that is suspended inside the bioreactor 105 or a separate unit (e.g., a unit outside the bioreactor 105). As shown in FIG. 1, the filter 110 occurs outside the bioreactor 105. The filter 110 can be a pipe containing multiple smaller tubes that include ultrafiltration membranes. In operation, the mixed liquor 109 exits the bioreactor 105 and flows through the multiple smaller tubes, filtering a fraction of the mixed liquor 109 that permeates the membrane (e.g., the permeate 112) while thickening the remaining sludge (e.g., the sludge 111). In some embodiments, the filter 110 is an ultrafilter with a 25-micron screen that allows a fraction of the mixed liquor 109 (e.g., the liquid and/or soluble constituents) to be filtered out as the permeate 112. The remaining contents of the mixed liquor 109 (e.g., the solids or the insoluble mass) are output as the sludge 111. In some embodiments, the permeate 112 includes trace amounts of suspended solids or insoluble mass. The thickness of the sludge 111 is determined by how much the mixed liquor 109 is dewatered by the filter 110 which can be effected by the pressure at which the mixed liquor 109 is introduced to the filter 110, the permeability of the filter 110, and/or the total area of the filter 110. The effect of the mixed liquor 109 on the permeability of the filter 110 is referred to as the filterability of the mixed liquor 109. As shown in FIG. 1, the sludge 111 can split into two streams, the return sludge 108 and the waste sludge 113. In some embodiments, a return line is positioned to direct the return sludge 108 from the filter 110 to the bioreactor 105. The return sludge 108 can be mixed with the liquid solution in the bioreactor 105. A waste line can be positioned to direct the waste sludge 113 from the filter 110 away from the bioreactor 105. The waste sludge 113 can be used to control a sludge retention time (SRT) in the bioreactor 105. This is advantageous to removing the mixed liquor 109 from the bioreactor 105 since the waste sludge 113 removes more insoluble mass per volume of liquid than the unfiltered mixed liquor 109. Thus, allowing less nutrients in the mixed liquor 109 to be lost. The use of SRT in regulating the return sludge 108 and the waste sludge 113 is discussed further herein.

In some embodiments, the controller 150 regulates the return sludge 108. More specifically, the controller 150 can regulate a return rate of the return sludge 108 to control the SRT (e.g., at least 15 days, 20 days, 30 days, 60 days, or 120 days, a range of 15-120 days, or any value therebetween). The SRT can be the rate and/or concentration at which insoluble mass (e.g., the bacterial biomass) is wasted from the bioreactor or the amount of time, on average, that insoluble mass remains in the bioreactor 105. The SRT can be equivalent to a product of the volume of liquid solution and the concentration of insoluble mass in the liquid solution divided by the product of the waste rate and the concentration of insoluble mass in the waste sludge 113. In some embodiments, the concentrations of insoluble mass in the liquid solution and in the waste sludge 113 are the same, and the SRT is equivalent to a volume of the liquid solution in the bioreactor divided by a waste rate of the waste sludge 113. In an MBR, the waste sludge 113 can be partially dewatered by the filter 110, so the concentration of insoluble mass in the waster sludge 113 can be greater than the concentration of insoluble mass in the liquid solution in the bioreactor 105. Additionally, or alternatively, the SRT can be equivalent to a volume of the liquid solution in the bioreactor divided by a remaining portion of the sludge that is not the return sludge 108. The controller 150 can also regulate a return rate of the return sludge 108 and/or a waste rate of the waste sludge 113 based on the measured pH of the liquid solution in the bioreactor 105. In some embodiments, the controller 150 regulates the return rate of the return sludge 108 and/or waste rate of the waste sludge 113 based on the mass flow of nitrogen and/or phosphorous of the feed 102 to the bioreactor 105. For example, the controller 150 can be used to keep a high waste rate of the waste sludge 113 to SRT ratio to help maintain the partial nitritation and/or complete nitratation environment (e.g., the partial nitrification environment) of the bioreactor 105. More specifically, the partial nitrification environment can be maintained by keeping the active population of bacteria (e.g., AOB and NOB) in the bioreactor 105 "young" by filtering out a high waste rate of waste sludge 113. In some embodiments, the controller 150 is configured to control the biological activity of the active population of bacteria (e.g., AOB and NOB) by regulating the number of bacteria, e.g., by utilizing a chemical inhibitor, ultraviolet light, rapid overheating, and/or laser. It is worth noting that mechanical methods of promoting cell death (e.g., ultraviolet light, laser, or rapid overheating) are less selective of the type of bacteria they kill and can result in dead bacteria in the liquid solution, which can reduce filterability of the mixed liquor 109. Chemical inhibitors are generally more selective of specific bacteria and can be used for chemical inhibition of AOB to reestablish process stability. For example, a chemical inhibitor can be introduced to the bioreactor 105 to inhibit AOB if the liquid solution contains high nitrite concentrations.

The SRT can be used to regulate sludge age of the return sludge 108. For example, the sludge age is preferably sufficient to avoid washing out the slowest-growing required microbes from a system, while also limiting the growth of undesirable faster-growing microbes or bacterial predators. For example, if the SRT is too high, then undesired slower-growing microbes or bacterial predators can grow in the bioreactor 105, thereby harming the active population of bacteria and preventing the partial nitrification process from occurring as expected. If the SRT is too low, then the active bacteria that were still growing may be lost, and thus less ammonium nitrate is produced during the partial nitrification process. The waste sludge 113 removes excess volume from the industrial system 100 and decreases the population of bacteria within the bioreactor 105 to keep pace with new bacteria growth at steady-state conditions. Balancing these factors can help ensure the bioreactor 105 operates in a predictable manner, such that the industrial system 100 is able to treat wastewater, maintain a pH balanced solution, and produce ammonium nitrate using biological activity. In some embodiments, a combination of low HRT and high SRT results in a substantial bacterial population in the bioreactor 105 capable of processing a generally higher ammonia load within a compact reactor volume while minimizing the need for biomass wasting to regulate the population of bacteria. As a result, the footprint of the system 100 is minimized, throughput is maximized, and the loss of ammonium nitrate to volume removed as waste is substantially reduced.

The RO unit 115 can be located downstream from the filter 110 and be positioned to receive the permeate 112 and output the retentate 114. The RO unit 115 can concentrate the permeate 112 into the retentate 114. The RO unit 115 can comprise a reverse osmosis filter including a semi-permeable membrane. The semi-permeable membrane can allow molecules of a certain size to pass through and can be particularly resistive to permeation by ions. For example, during a water desalination process, in which salt water is pumped through RO filters, the semi-permeable membrane can allow small water molecules to pass through while limiting the salt ions from flowing through. As such, the RO unit 115 can concentrate a high-strength ammonium nitrate solution (e.g., the retentate 114), e.g., by preferentially allowing water molecules to pass through the semi-permeable membranes while holding back ammonium and nitrate ions. Thus, the outlet of the retentate 114 is a higher concentration of ammonium nitrate solution than the inlet stream of the permeate 112. For example, the RO unit 115 can be positioned to receive the permeate 112, e.g., at a concentration of at least 2000 ppm and output the retentate 114, at a concentration of 4% ammonium nitrate nitrogen (e.g., 40,000 ppm). Performance of the RO unit 115 can be maintained by monitoring temperature, crossflow velocity, and membrane conditions. In some embodiments, a fraction of the ammonium and nitrate ions are lost when passing through the semi-permeable membrane of the RO unit 115. The ions lost to the RO unit 115 can be minimized by incorporating multiple stages of RO. For example, RO can be done in one or more passes to concentrate the permeate 112 into the retentate 114.

In some embodiments, it is desirable to reduce COD within the industrial system 100. Reducing COD can benefit any downstream concentration equipment, where soluble organics pose a fouling risk (e.g., at the ultrafilter 110 and/or the RO unit 115). Increased influent COD can occur based on the composition of the feed 102. For example, COD levels can increase if the feed 102 contains high content of soluble non-biodegradable organics (e.g., the fraction of COD that is not BOD, and thus, is unaffected by the bioreactor 105). Increased COD levels can lead to decreased efficiency, increased energy consumption, and potential equipment failures throughout the industrial system 100.

In some embodiments, the permeate 112 and/or the retentate 114 do not include AOB or NOB from the bioreactor 105. Additionally or alternatively, the permeate 112 and/or the retentate 114 can be used for organic crop production, e.g., under the U.S. Department of Agriculture National Organic Program. In some embodiments, the industrial system 100 uses partial nitritation and complete nitratation facilitated by AOB and NOB to produce nitrate biologically without additional alkalinity. Doing so can make it easier for products to obtain desirable organic classifications, as the high alkalinity and use of chemicals may be prevented from being used, as is in traditional WWTP products for organic crop production.

The evaporator 120 can be located downstream from the RO unit 115 and can be configured to receive the retentate 114 and output of the concentrated product 116. The evaporator 120 can be used to increase the concentration of the retentate 114 into the concentrated product 116. For example, the retentate 114 received by the evaporator 120 can have a concentration of at least 2%, 3%, 4%, 5%, or 6% ammonium nitrate nitrogen, a range of 2-6% ammonium nitrate nitrogen, or any value therebetween, and the concentrated product 116 can have a concentration of at least 7%, 12%, 16%, 20%, or 22% ammonium nitrate nitrogen, a range of 7-22% ammonium nitrate nitrogen, or any value therebetween. The evaporator 120 can include a heat source that comes in contact with the retentate 114, causing excess water to evaporate from the retentate 114 and thereby concentrate the ammonium nitrate. At the temperatures required to evaporate water (e.g., 100° C.), nitrogen loss can occur. However, most of the nitrogen loss in the evaporator 120 is nitrite loss, which is readily decomposed and lost as a vapor at said temperatures. Loss of ammonia can also occur, which stabilizes the ammonia by increasing the fraction of ammonia as ammonium. However, since the retentate 114 lacks other pH buffers, a small amount of volatilized ammonia results in a significant decline in the pH of the concentrated product 116. For example, in operation, the evaporated fluid leaving the evaporator 120 can have a pH value of approximately 3 (e.g., lower than the near neutral pH that is preferred). A small amount of aqueous ammonia can be used to bring the concentrated product 116 back to the near-neutral pH. Nevertheless, if nitrite accumulation is minimized (e.g., by promoting an environment that favors nitratation relative to nitritation throughout the industrial system 100), evaporation losses of nitrogen and ammonia and pH adjustments are not significant.

The aqueous ammonia can be collected in a parallel ammonia recovery system (not illustrated). The parallel ammonia recovery system can include mass transfer towers designed to recover ammonia lost in the evaporated fluid leaving the evaporator 120 or in any other component of the industrial system 100 (e.g., ammonia lost in the bioreactor 105). The aqueous ammonia can be used for final pH adjustment of the concentrated product 116 or as a part of the feed 102 to the bioreactor 105. The parallel ammonia recovery system can include a distillation column and a scrubbing unit downstream of the distillation column. The distillation column can have multiple inlet streams of liquid ammonia and vapor ammonia captured from the evaporator 120. The liquid ammonia and vapor ammonia from the evaporator 120 can be a concentrated form of ammonium that is suitable for pH adjustments. Additionally or alternatively, the liquid ammonia and vapor ammonia from the evaporator 120 can be distilled into a liquid ammonia that can be reintroduced into the industrial system 100. The liquid ammonia can be reintroduced into the concentrated product 116 (e.g., to adjust pH), or it can be reintroduced into the bioreactor 105 (e.g., via the feed 102). The distillation column can further include an outlet of vapor ammonia directed to the scrubbing unit. The scrubbing unit can further include an inlet stream of liquid ammonium nitrate captured from the bioreactor 105 or the filter 110 (e.g., a less concentrated ammonium nitrate). The scrubbing unit can dilute the inlet streams into a liquid ammonia suitable to be reintroduced into the bioreactor 105 (e.g., in the feed 102). The remaining vapor ammonia from the scrubbing unit can be expelled back into the environment. Thus, the parallel ammonia recovery system can recover and process evaporated ammonia and less concentrated ammonium nitrate throughout the industrial system 100, thereby reducing the total amount of ammonia lost to the environment.

The resulting concentrated product 116 can qualitatively have a distinct odor, though it is not offensive or strong in comparison to the odor of ammonia in the feed 102 (despite having a many-times greater concentration), nor does the odor resemble the odor of ammonia in the feed 102. The concentrated product 116 can be a dark caramel, transparent liquid and/or can have low turbidity. The concentrated product 116 can also have a stability such that it can be stored (e.g., for at least one month, two months, three months, or six months, a range of one to six months, or any value therebetween) with no settling, clarifying, or measurable decrease in product concentration.

It is worth noting that although FIG. 1 shows the industrial system 100 with the bioreactor 105 upstream from the filter 110, the RO unit 115, and the evaporator 120, the industrial system 100 can include the components in a different order. For example, the filter 110, the RO unit 115, and the evaporator 120 can be housed in a singular housing that does not have visible inlets and outlets from one component to the next.

Figure 2:
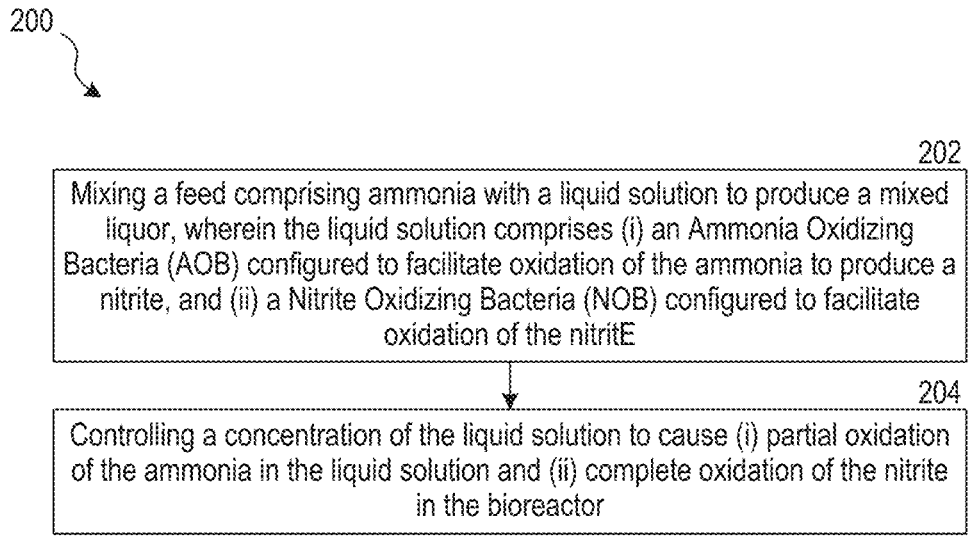
FIGS. 2 and 3 are flow diagrams illustrating methods for producing ammonium nitrate, in accordance with embodiments of the present technology.

FIG. 2 is a flow diagram illustrating a method 200 for producing ammonium nitrate, in accordance with embodiments of the present technology. The method 200 can include mixing a feed comprising ammonia with a liquid solution to produce a mixed liquor, wherein the liquid solution compresses (i) AOB configured to facilitate oxidation of the ammonia to produce a nitrite, and (ii) NOB configured to facilitate oxidation of the nitrite (process portion 202). The liquid solution including the ammonia, the AOB, and the NOB are described herein (e.g., with reference to FIG. 1).

The method 200 can further comprise controlling a concentration of the liquid solution to cause (i) partial oxidation of the ammonia in the liquid solution and (ii) complete oxidation of the nitrite in the bioreactor (process portion 204). The partial oxidation of ammonia in the liquid solution is referred to as partial nitritation. The AOB, as described in process portion 202, can facilitate oxidation of the ammonia to produce a nitrite at a nitritation rate in the bioreactor. The complete oxidation of the nitrite in the bioreactor is referred to as complete nitratation. The NOB, as described in process portion 202, can facilitate oxidation of the nitrite to produce a mixed liquor comprising a nitrate at a nitratation rate in the bioreactor. Further, the method utilizes partial nitritation and complete nitratation to create an environment that favors nitratation (e.g., the rate of nitrite oxidation is greater than the rate of ammonia oxidation). Since the system favors complete nitratation and partial nitritation; however, the liquid solution of the bioreactor can have a greater amount of AOB by mass than NOB by mass. The growth rates of active bacteria (e.g., AOB and NOB) also affects partial nitrification. For example, in a system that favors partial nitrification, the non-substrate limited growth rate of the NOB should grow at a rate of at least one order of magnitude of the non-substrates limited rate of AOB. In some embodiments, the growth rate of NOB only exceeds the growth rate of AOB marginally, but because wasting is done to regulate the AOB population, the AOB in the bioreactor can be insufficient to regulate the faster-growing NOB population. This can eventually lead to the NOB population limiting itself by consuming nitrite until low nitrite availability limits the growth rate of the NOB population. The growth rate and/or amount of active bacteria in the bioreactor can further be controlled by adjusting pH, DO, temperature, feed rates, recycle rates, and waste rates to maintain a partial nitrification environment. For example, the partial nitrification environment can be maintained by regulating the active population of bacteria in the bioreactor. In addition, a high wasting rate can remove inert endogenous products that otherwise accumulate in the bioreactor, as well as dead cells and solids that blow in from the atmosphere.

Figure 3:
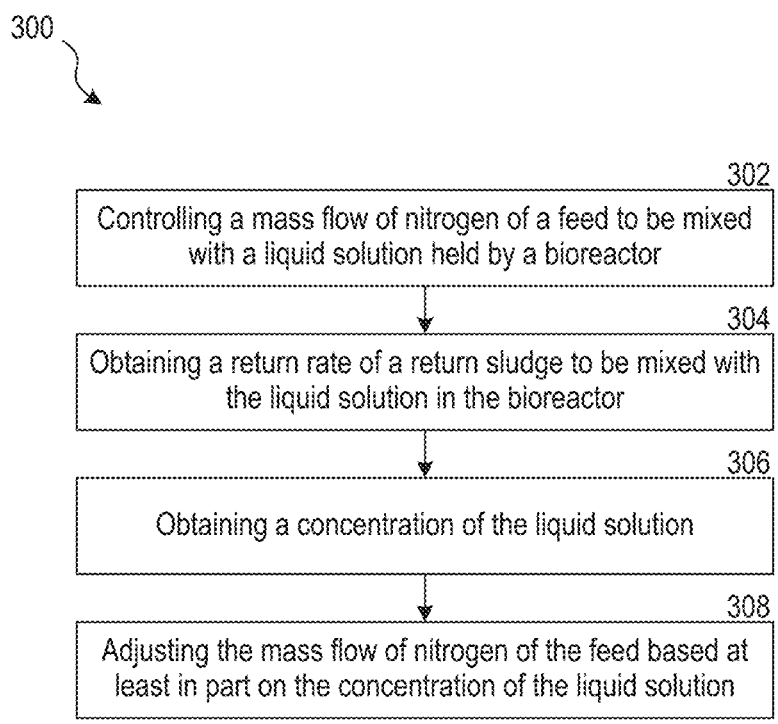

FIG. 3 is a flow diagram illustrating a method 300 for producing ammonium nitrate via a bioreactor, in accordance with embodiments of the present technology. The method 300 can include controlling a mass flow of nitrogen and/or phosphorous of a feed to be mixed with a liquid solution held by a bioreactor (process portion 302). The mass flow of nitrogen and/or phosphorous to be mixed with the liquid solution of the bioreactor is controlled by a feed rate, which can be regulated by the controller as described herein (e.g., with reference to FIG. 1).

The method 300 can further comprise obtaining a return rate of a return sludge to be mixed with the liquid solution in the bioreactor (process portion 304). The return rate of the return sludge can be regulated by the controller based on the desired retention time. In some embodiments, a return line is positioned to direct a portion of the sludge from the filter to the bioreactor. For example, the return sludge can be directed by the return line to be mixed with the liquid solution in the bioreactor at the return rate. In some embodiments, the return rate is determined based on a concentration of the sludge and/or a feed rate of the bioreactor (as described in process portion 302).

The method 300 can further comprise obtaining a concentration of the liquid solution (process portion 306). One or more sensors ("sensor(s)") can be used to determine the concentration of the liquid solution in the bioreactor. As described in FIG. 1, the sensor(s) can measure the pH, DO, and/or temperature of the liquid solution in the bioreactor. The sensor(s) can be coupled to the controller to regulate the concentration of the liquid solution based on the concentration obtained via the sensor(s).

The method 300 can further comprise adjusting the mass flow of nitrogen and/or phosphorous of the feed based at least in part on the concentration of the liquid solution (process portion 308). The controller can open and/or close the valves based on the pH and/or concentration of the liquid solution of the bioreactor, as determined in process portion 306. As described in FIG. 1, the controller can be operably coupled to the sensor(s) used to determine the concentration of the liquid solution. In addition, the controller can be operably coupled to the valves that can be opened or closed to adjust the mass flow of nitrogen and/or phosphorous of the base feed into the bioreactor, and thus, adjust the concentration of the liquid in the bioreactor.

Figure 4:
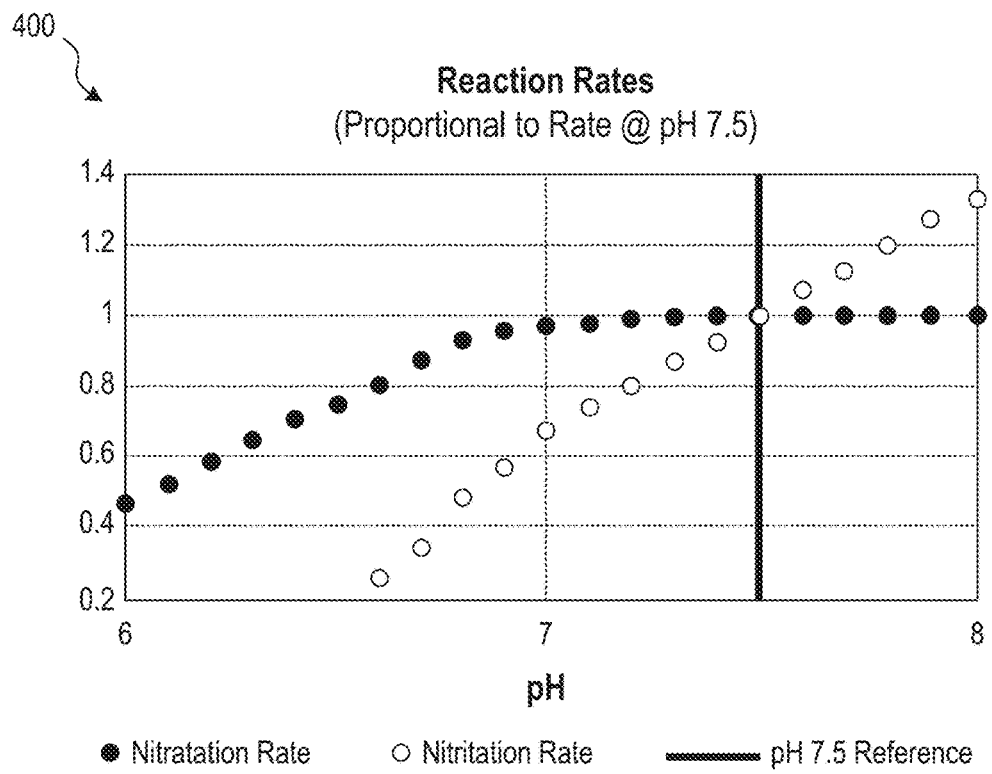
FIG. 4 illustrates a graph of a nitritation reaction rate and a nitratation reaction rate relative to pH, in accordance with embodiments of the present technology.

FIG. 4 illustrates a graph 400 of a nitritation reaction rate and a nitratation reaction rate relative to pH, in accordance with embodiments of the present technology. The reaction rates, as shown in FIG. 4, assume a fixed temperature, that oxygen, carbon dioxide, nitrogen, phosphorus, and all micronutrients are not limiting, no other chemical inhibitors are present, a fixed ammonia concentration, a fixed nitrite concentration (e.g., high enough that nitrite is not a limiting substrate), a fixed AOB concentration, and a fixed NOB concentration. As shown in FIG. 4, the nitratation reaction rate and nitritation reaction rate are proportional rates at a pH of 7.5 (shown as the intersection at the vertical black line). However, embodiments of the present technology favor increased nitratation reactions to nitritation reactions, thus driving an operative pH of at most 6.0, 6.5, 7.0, or 7.5, a range of 6.0-7.5, or any value therebetween at which nitratation and nitritation rates are approximately equal, as described in more detail with reference to FIG. 1. The lower operative pH favors nitrite oxidation into nitrate over ammonia oxidation into nitrite, referred to herein as partial nitrification (e.g., partial nitritation and complete nitratation). This pH can allow NOB to reduce nitrite concentration until the NOB are limited by low nitrite availability. In addition, the partial oxidation of ammonia (e.g., partial nitritation) can leave residual ammonia and/or ammonium in the liquid solution of the bioreactor, as described in FIG. 1, which acts as a buffer to maintain the lower operative pH.

In some embodiments, the sensor(s) of the bioreactor measure the pH of the liquid solution of the bioreactor. Additionally or alternatively, the sensor(s) can be coupled to the controller to maintain a target range pH of 4.0-7.0, or any value therebetween, to favor nitrite oxidation into nitrate. For example, if the liquid solution of the bioreactor has a pH outside the target range, the controller can be used to regulate the mass flow of nitrogen and/or phosphorous of the feed to the bioreactor to maintain the target range pH. Additionally or alternatively, the regulation of the mass flow of nitrogen and/or phosphorous of the feed to the bioreactor based on a measured pH and/or concentration can promote partial nitrification within the bioreactor.

Although pH sensors can be used to monitor nitritation reaction rates and a nitratation reaction rates, the bioreactor can also include sensors that monitor the oxygen levels (e.g., DO levels) and the temperature of the liquid solution of the bioreactor. As described in more detail with reference to FIG. 1, the controller can be configured to regulate multiple factors influencing the nitratation reaction rate and nitritation reaction rates in the bioreactor (e.g., oxygen levels, temperature, wasting rate of the bacteria, hydraulic residence time, and/or SRT) in addition to controlling the mass flow of nitrogen (or ammonia) and/or phosphorous (or unprocessed manure) in the feed. In a preferred embodiment, the growth rate of NOB should exceed the growth rate of AOB by an order of magnitude until NOB becomes substrate-limited. In some embodiments, the growth rate of NOB only exceeds the growth rate of AOB marginally, but because wasting is done to regulate the AOB population, the AOB in the bioreactor is insufficient to regulate the faster-growing NOB population. Additionally or alternatively, it can be expected that the population of heterotrophic bacteria (e.g., AOB and NOB) are to operate at substrate-limited conditions (e.g., to the point of being limited by the availability of soluble biodegradable organics). For example, oxygen is a limiting substrate analogous to ammonia for AOB and nitrite for NOB and can be used to evaluate the performance of the heterotrophic bacteria in the bioreactor. For example, if the system has low C:N ratios (e.g., an environment that favors partial nitrification), there should be a nearly complete BOD reduction. In some embodiments, the C:N ratio is at most 1:1, 5:1, 10:1, 15:1, or 20:1, a range of 1-20:1, or any value therebetween, such that carbonaceous BOD is limited, thereby limiting growth of the heterotrophic bacteria that consume ammonia nitrogen. Additionally or alternatively, the C:N ratio can be 0.

Figure 5:
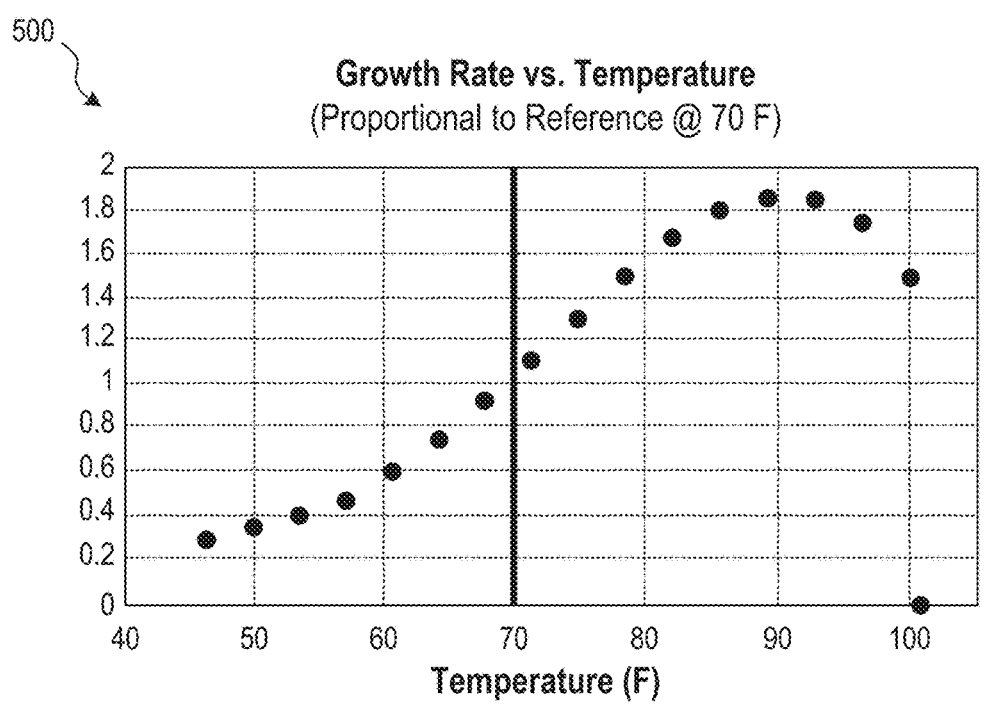
FIG. 5 illustrates a graph of nitrifier growth rate within a bioreactor relative to temperature, in accordance with embodiments of the present technology.

FIG. 5 illustrates a graph 500 of a growth rate of nitrifiers (e.g., AOB and NOB) within a bioreactor relative to temperature, in accordance with embodiments of the present technology. The graph shows a nitrifier growth rate of 1 at a temperature of 70 degrees Fahrenheit. The growth rate equal to 1 is indicative of the point of normalization and is arbitrarily selected to equal room temperature. It is worth noting that growth rates of AOB and NOB are not necessarily corresponding to one another at this temperature.

Figure 6:
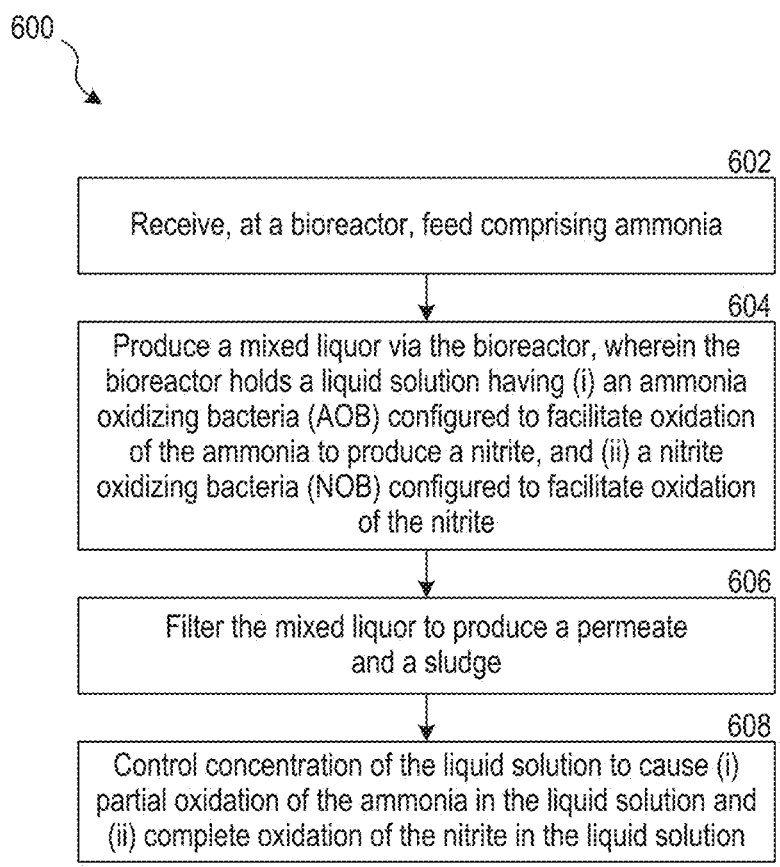
FIG. 6 is a flow diagram illustrating a method for producing ammonium nitrate, in accordance with embodiments of the present technology.

FIG. 6 is a flow diagram illustrating a method 600 for producing ammonium nitrate via a bioreactor, in accordance with embodiments of the present technology. The method 600 can be performed in combination with one or more process portions of the methods 200 and/or 300 described in FIGS. 2 and 3, respectively, and/or any of the other methods or process portions described herein. Additionally or alternatively, the method 600 can be performed using one or more components of the system 100 described in more detail with reference to FIG. 1.

The method 600 can include receiving, at a bioreactor, a feed comprising ammonia (process portion 602). In some embodiments, the bioreactor is the bioreactor 105, and the feed is the feed 102 described in more detail with reference to FIG. 1. The feed can be ammonia-rich, serving as an initial input for biological processes within the bioreactor. For example, the ammonia in the feed can be a substrate for microorganisms within the bioreactor to undergo a partial nitrification process. In some embodiments, the startup of a partial nitrification system can be particularly challenging if there is an insufficient initial population of nitrifying bacteria to immediately begin partial nitrification and/or if the reactor starts in water that already contains ammonia. To address this, the method 600 can include introducing a feed of organic sodium bicarbonate as an alkalinity source to support complete nitrification before adding ammonia, while not adding additional alkalinity. Over time, the alkalinity can wash out of the system, causing the pH to drop. Once the pH drops, stable partial nitrification can commence, provided biological stability of the system is maintained. One or more processes for maintaining biological stability of the system are described in more detail with reference to process portion 608.

In some embodiments, the method 600 includes producing a mixed liquor via the bioreactor. Specifically, the bioreactor can hold a liquid solution containing AOB configured to facilitate the oxidation of ammonia to produce nitrite and NOB configured to facilitate the oxidation of nitrite (process portion 604). The AOB can convert the ammonia in the feed into nitrite, while the NOB can further oxidize the nitrite into nitrate, resulting in a liquid solution containing the bacteria and the intermediate and final products of their metabolic processes. In doing so, the bioreactor can produce a mixed liquor comprising nitrate. The mixed liquor can be the mixed liquor 109 described in more detail with reference to FIG. 1. A controller operably coupled to the bioreactor (e.g., the controller 150 of FIG. 1) can support the growth and activity of the AOB and the NOB, and in turn, the production of the mixed liquor, by monitoring and/or adjusting the pH and/or concentrations of the liquid solution, as described in more detail herein with reference to process portion 608.

The method 600 can further include filtering the mixed liquor to produce a permeate and a sludge (process portion 606). The permeate can be the permeate 112, and the sludge can be the sludge 111 described in more detail with reference to FIG. 1. In some embodiments, the permeate is a filtered liquid containing dissolved substances, and the sludge is concentrated biomass and particulate matter resulting from filtering the mixed liquor through a filter (e.g., the filter 110 of FIG. 1). The sludge can be removed from the system (e.g., as the waste sludge 113 of FIG. 1) and/or recirculated to the bioreactor (e.g., as the return sludge 108 of FIG. 1). For example, a portion of the biomass within the sludge can be recirculated to the bioreactor to maintain biological activity, while the permeate can be further processed to produce the ammonium nitrate. The controller described herein can be further configured to regulate the return rate of the return sludge based on a desired SRT or sludge age. For example, the SRT can be at least 15 days, 20 days, 30 days, 60 days, or 120 days, a range of 15 and 120 days, or any value therebetween. Additionally or alternatively, the controller can be configured to regulate the waste rate of the waste sludge and/or permeate such that the liquid solution of the bioreactor can have an HRT, or the time the liquid solution remains in the bioreactor, of at most 0.5 days, 1 day, 5 days, 10 days, or 20 days, a range of 0.5 days and 20 days, or any value therebetween. In some embodiments, the method 600 includes regulating the return rate of the return sludge and the waste rate of the waste sludge such that the sum of the waste rate of the waste sludge and the flow rate of the permeate is less than the sum of the return rate of the return sludge and the flow rate of the feed. Additionally or alternatively, the method 600 can include regulating the return rate of the return sludge and the waste rate of the waste sludge such that the waste rate of the waste sludge is less than the return rate of the return sludge.

The method 600 can further include adjusting a temperature of the return sludge using a heat exchanger. For example, the controller can be operably coupled to the heat exchanger and/or a temperature sensor in the liquid solution of the bioreactor such that the controller can adjust the temperature of the return sludge to maintain or adjust the temperature of the liquid solution in the bioreactor. Additionally or alternatively, the method 600 can include introducing air to the bioreactor using a blower. The controller can be operably coupled to the blower and/or an oxygen sensor measuring oxygen and/or dissolved oxygen in the bioreactor such that the controller can adjust operation of the blower based at least in part on the measured oxygen in the bioreactor.

In some embodiments, the method includes controlling the concentration of the liquid solution in the bioreactor to cause partial oxidation of ammonia and complete oxidation of nitrite in the liquid solution (process portion 608). As described herein, a controller operably coupled to the bioreactor can monitor and/or adjust the pH and/or concentrations of the liquid solution to maintain the stability of the biological components (e.g., the AOB and the NOB) in the bioreactor. In some embodiments, one or more sensors are positioned within the bioreactor to monitor the conditions of the liquid solution. More specifically, the sensors can measure the pH of the liquid solution, the concentration of ammonia, ammonium, phosphate, phosphorus, nitrate, and/or nitrite in the liquid solution, and/or the like.

In some embodiments, the method 600 comprises controlling biological activity by regulating the pH of the liquid solution. For example, the controller can be configured to regulate the mass flow of nitrogen and/or phosphorus of the feed to the bioreactor to maintain the pH of the liquid solution within a range of 4.0-7.0. In some embodiments, the biological activity is controlled by regulating the pH of the liquid solution to be at most 6.5, 6.6, 6.7, 6.8, 6.9, or 7.0, a range of 6.5 to 7.0, or any value therebetween. Additionally or alternatively, the biological activity can be controlled by regulating the pH of the liquid solution to be at most 4.0, 4.5, 5.0, 5.5, or 6.0, a range of 4.0 to 6.0, or any value therebetween. The method 600 can further comprise controlling biological activity by regulating the phosphate concentration of the liquid solution. For example, the biological activity can be controlled by regulating the phosphate concentration in the bioreactor to be at least 0.1, 0.3, 0.5, 0.7, or 1.0 ppm, a range of 0.1 to 1.0 ppm, or any value therebetween. In some embodiments, the controller is configured to adjust the pH and/or concentrations of the liquid solution by, for example, regulating the wasting rate and/or return rate of the sludge in the system, adjusting the mass flow of nitrogen and/or phosphorus of the feed directed into the bioreactor, and/or utilizing a chemical inhibitor, ultraviolet light, and/or a laser to regulate the amount of AOB and/or NOB within the bioreactor.

Additionally or alternatively, the controller can be configured to maintain a partial nitrification environment within the system such that the bioreactor can be operated with a low wasting rate and/or high return sludge rate, resulting in a generally larger population of bacteria in the liquid solution of the bioreactor operating under inhibited conditions. For the AOB, inhibition can manifest as a lower pH, while for the NOB, inhibition can manifest as very low residual nitrite concentrations. In some embodiments, a measured concentration of nitrite in the liquid solution of the bioreactor can be at most 50, 100, 200, or 400 parts per billion (ppb), a range of 50 to 400 ppb, or any value therebetween. The controller can be configured to manage sudden increases in ammonia loading (e.g., from the feed 102), which can increase the pH of the liquid solution, thereby relieving some of the pH inhibition of AOB and allowing the AOB to meet the increased oxidation demand of the liquid solution in the bioreactor. The increase in nitrite production can raise nitrite concentration. However, since the NOB are greatly inhibited by substrate scarcity, the nitrite concentration can only increase marginally before the NOB meets the increased oxidation demand. When the load decreases, both pH and nitrite concentration can decrease, inhibiting both AOB and NOB but allowing both populations to persist due to the reversible nature of AOB and NOB inhibition. In some embodiments, the controller can regulate the rate of ammonia loading change to not outpace the rate at which the metabolism of both AOB and NOB can activate as inhibitions are relieved, leveraging the inherent stability of the bioreactor to absorb fluctuations in ammonia loading. Additionally or alternatively, the controller can regulate conditions in the bioreactor such that mass flow of nitrogen and/or phosphorus of the feed corresponds to the current metabolic rate of the AOB.

In some embodiments, the method 600 includes regulating the system to inhibit the rate of nitritation relative to the rate of nitratation within the bioreactor and/or to promote the rate of nitratation relative to the rate of nitritation within the bioreactor and/or to promote non-complete nitritation and complete nitratation within the bioreactor. For example, the controller can regulate the mass flow of nitrogen and/or phosphorus of the feed to the bioreactor such that nitrite production via AOB does not outpace the capacity of NOB to oxidize nitrite, thereby maintaining the stability of the system. In some embodiments, the relationship between pH and/or nitrite concentration in the bioreactor can define the boundary of the system's stability criterion. For example, the pH and/or nitrite relationship within the bioreactor can be used to control the mass flow of nitrogen and/or phosphorus of the feed based on how the current pH of the bioreactor falls within those stability criteria. In some embodiments, a higher pH setpoint results in a greater growth rate of both AOB and NOB at the cost of less stability, while a lower pH setpoint results in a slower growth rate and greater stability. The controller can monitor and adjust the pH of the liquid solution in the bioreactor such that changes in the pH setpoint, especially increases in pH, occur slowly enough to maintain the stability of the biological activity within the bioreactor.

As described herein, the stability criteria of partial nitrification can be that nitrite production by AOB, AOB catabolism, and/or AOB growth rate generally do not exceed the maximum capacity of NOB to oxidize nitrite. When nitrite concentration is low enough that substrate availability can limit NOB growth, then as nitrite production increases, the capacity of NOB to oxidize nitrite can increase, and the NOB population can also grow faster, eventually reducing nitrite concentration. If nitrite concentration exceeds a threshold (e.g., pH dependent), inhibition of NOB by free nitrous acid can reduce the capacity of NOB to oxidize nitrite. In this condition, if nitrite production remains constant, nitrite can accumulate, initially slowly but increasingly faster as NOB activity becomes more inhibited by the rising concentration. If ammonia loading, and therefore nitrite production, is decreased quickly enough, recovery to the setpoint stability can occur, as the nitrite production rate can drop below the rate at which nitrite is oxidized. Recovery can become slower the longer nitrite accumulates, and past a certain point, recovery can become infeasible. Given enough time and a high enough wasting rate, the NOB can be washed out of the system, resulting in the bioreactor having only AOB converting ammonia to nitrite, otherwise referred to as partial nitritation. By maintaining partial nitrification conditions, particularly by maintaining the stability of the biological activity within the liquid solution of the bioreactor, the method 600 can be used to consistently produce ammonium nitrate and/or permeate that can be further processed to produce ammonium nitrate, as described in more detail with reference to concentrating the permeate 112 of FIG. 1.

III. Conclusion

It will be apparent to those having skill in the art that changes may be made to the details of the above-described embodiments without departing from the underlying principles of the present technology. In some cases, well known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Throughout this disclosure, the singular terms "a," "an," and "the" include plural referents unless the context clearly indicates otherwise. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

Unless otherwise indicated, all numbers expressing numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims. As used herein, the term "and/or," as in "A and/or B" refers to A alone, B alone, or both A and B.

The present technology is illustrated, for example, according to various aspects described below as numbered clauses (1, 2, 3, etc.) for convenience. These are provided as examples and do not limit the present technology. It is noted that any of the dependent clauses may be combined in any combination, and placed into a respective independent clause. The other clauses can be presented in a similar manner.

1. An industrial system for producing ammonium nitrate using biological activity, the system comprising:
   a bioreactor positioned to receive a feed comprising ammonia, wherein the bioreactor is configured to hold a liquid solution including (i) an ammonia oxidizing bacteria (AOB) configured to facilitate oxidation of the ammonia to produce a nitrite at a nitritation rate, and (ii) a nitrite oxidizing bacteria (NOB) configured to facilitate oxidation of the nitrite at a nitratation rate to produce a mixed liquor comprising a nitrate;
   a filter positioned to (i) receive the mixed liquor and (ii) produce a permeate and a sludge;
   a sensor positioned to measure a concentration of the liquid solution of the bioreactor; and
   a controller operably coupled to the sensor, wherein the controller is configured to control biological activity within the bioreactor based on the measured concentration of the liquid solution to produce ammonium nitrate.

2. The system of any one of the clauses herein, wherein the controller is configured to control the biological activity by regulating a wasting rate of the sludge.

3. The system of any one of the clauses herein, wherein the controller is configured to control the biological activity by regulating a mass flow of phosphorous of the feed.

4. The system of any one of the clauses herein, wherein the controller is configured to control the biological activity by regulating a mass flow of phosphorous of the feed utilizing unprocessed manure.

5. The system of any one of the clauses herein, wherein the controller is configured to control the biological activity by regulating a mass flow of nitrogen of the feed.

6. The system of any one of the clauses herein, wherein the controller is configured to control the biological activity by regulating a mass flow of nitrogen and/or phosphorus of the feed.

7. The system of any one of the clauses herein, wherein the controller is configured to control the biological activity by regulating a mass flow of nitrogen of the feed corresponds to a metabolic rate of the AOB.

8. The system of any one of the clauses herein, wherein the controller is configured to control the biological activity by regulating an amount of the AOB and/or the NOB utilizing a chemical inhibitor, ultraviolet light, and/or a laser.

9. The system of any one of the clauses herein, wherein the sensor is a pH sensor positioned to measure a pH of the liquid solution, and wherein the controller is configured to regulate a mass flow of nitrogen and/or phosphorus of the feed to the bioreactor based on the measured pH of the liquid solution.

10. The system of any one of the clauses herein, wherein the sensor is a phosphate sensor positioned to measure a phosphate concentration of the liquid solution, and wherein the controller is configured to regulate a mass flow of nitrogen and/or phosphorus of the feed to the bioreactor based on the measured phosphate concentration of the liquid solution.

11. The system of any one of the clauses herein, wherein the sensor is a phosphorous sensor positioned to measure a phosphorous concentration of the liquid solution, and wherein the controller is configured to regulate a mass flow of nitrogen and/or phosphorus of the feed to the bioreactor based on the measured phosphorous concentration of the liquid solution.

12. The system of any one of the clauses herein, wherein the sensor is an ammonia sensor positioned to measure an ammonia concentration of the liquid solution, and wherein the controller is configured to regulate a mass flow of nitrogen and/or phosphorus of the feed to the bioreactor based on the measured ammonia concentration of the liquid solution.

13. The system of any one of the clauses herein, wherein the sensor is an ammonium sensor positioned to measure an ammonium concentration of the liquid solution, and wherein the controller is configured to regulate a mass flow of nitrogen and/or phosphorus of the feed to the bioreactor based on the measured ammonium concentration of the liquid solution.

14. The system of any one of the clauses herein, wherein the sensor is a nitrate sensor positioned to measure a nitrate concentration of the liquid solution, and wherein the controller is configured to regulate a mass flow of nitrogen and/or phosphorus of the feed to the bioreactor based on the measured nitrate concentration of the liquid solution.

15. The system of any one of the clauses herein, wherein the sensor is a nitrite sensor positioned to measure a nitrite concentration of the liquid solution, and wherein the controller is configured to regulate a mass flow of nitrogen and/or phosphorus of the feed to the bioreactor based on the measured nitrite concentration of the liquid solution.

16. The system of any one of the clauses herein, wherein the sensor is a pH sensor positioned to measure a pH of the liquid solution, and wherein the controller is configured to regulate a mass flow of nitrogen and/or phosphorus of the feed to the bioreactor based on the measured pH by maintaining the pH of the liquid solution at most 6.5, 6.6, 6.7, 6.8, 6.9, or 7.0.

17. The system of any one of the clauses herein, wherein the sensor is a pH sensor positioned to measure a pH of the liquid solution, and wherein the controller is configured to regulate a mass flow of nitrogen and/or phosphorus of the feed to the bioreactor based on the measured pH by maintaining the pH of the liquid solution at most 7.0.

18. The system of any one of the clauses herein, wherein the sensor is a pH sensor positioned to measure a pH of the liquid solution, and wherein the controller is configured to regulate a mass flow of nitrogen and/or phosphorus of the feed to the bioreactor based on the measured pH by maintaining the pH of the liquid solution between 6.5 and 7.0.

19. The system of any one of the clauses herein, wherein the sensor is a pH sensor positioned to measure a pH of the liquid solution, and wherein the controller is configured to regulate a mass flow of nitrogen and/or phosphorus of the feed to the bioreactor based on the measured pH by maintaining the pH of the liquid solution at most 4.0, 4.5, 5.0, 5.5, and 6.0.

20. The system of any one of the clauses herein, wherein the sensor is a pH sensor positioned to measure a pH of the liquid solution, and wherein the controller is configured to regulate a mass flow of nitrogen and/or phosphorus of the feed to the bioreactor based on the measured pH by maintaining the pH of the liquid solution at most 6.0.

21. The system of any one of the clauses herein, wherein the sensor is a pH sensor positioned to measure a pH of the liquid solution, and wherein the controller is configured to regulate a mass flow of nitrogen and/or phosphorus of the feed to the bioreactor based on the measured pH by maintaining the pH of the liquid solution between 4.0 and 6.0.

22. The system of any one of the clauses herein, wherein the sensor is a pH sensor positioned to measure a pH of the liquid solution, and wherein the controller is configured to regulate a mass flow of nitrogen and/or phosphorus of the feed to the bioreactor based on the measured pH by maintaining the pH of the liquid solution within a range of 4.0-7.0, 5.6-6.9, 5.7-6.8, 5.8-6.7, 5.9-6.6, or 6.0-6.5.

23. The system of any one of the clauses herein, wherein the sensor is a pH sensor positioned to measure a pH of the liquid solution, and wherein the controller is configured to regulate a mass flow of nitrogen and/or phosphorus of the feed to the bioreactor based on the measured pH by maintaining the pH of the liquid solution within a range of 4.0-7.0.

24. The system of any one of the clauses herein, wherein regulating a mass flow of nitrogen and/or phosphorus of the feed to the bioreactor is based on the measured concentration (i) inhibiting the rate of nitritation relative to the rate of nitratation within the bioreactor, and/or (ii) promoting the rate of nitratation relative to the rate of nitritation within the bioreactor.

25. The system of any one of the clauses herein, wherein regulating a mass flow of nitrogen and/or phosphorus of the feed to the bioreactor is based on the measured concentration promoting non-complete nitritation and complete nitratation within the bioreactor.

26. The system of any one of the clauses herein, wherein regulating a mass flow of nitrogen and/or phosphorus of the feed to the bioreactor is based on the measured concentration converting and/or oxidizing at most 40%, 45%, 50%, 55%, or 60% of the ammonia.

27. The system of any one of the clauses herein, wherein regulating a mass flow of nitrogen and/or phosphorus of the feed to the bioreactor is based on the measured concentration converting and/or oxidizing at most 60% of the ammonia.

28. The system of any one of the clauses herein, wherein regulating a mass flow of nitrogen and/or phosphorus of the feed to the bioreactor is based on the measured concentration converting and/or oxidizing between 40% and 60% of the ammonia.

29. The system of any one of the clauses herein, wherein regulating a mass flow of nitrogen and/or phosphorus of the feed to the bioreactor is based on the measured concentration of nitrite nitrogen (NO2-N) left unoxidized being at most 0.1, 1, 10, 25, or 50 parts per million (ppm) nitrite nitrogen.

30. The system of any one of the clauses herein, wherein regulating a mass flow of nitrogen and/or phosphorus of the feed to the bioreactor is based on the measured concentration of nitrite nitrogen (NO2-N) left unoxidized being at most 0.1 parts per million (ppm) nitrite nitrogen.

31. The system of any one of the clauses herein, wherein regulating a mass flow of nitrogen and/or phosphorus of the feed to the bioreactor is based on the measured concentration of nitrite nitrogen (NO2-N) left unoxidized being between 0.1 and 50 parts per million (ppm) nitrite nitrogen.

32. The system of any of the clauses herein, wherein the measured concentration of nitrite in the liquid solution of the bioreactor is at most 50, 100, 200, or 400 parts per billion (ppb).

33. The system of any of the clauses herein, wherein the measured concentration of nitrite in the liquid solution of the bioreactor is at most 100 parts per billion (ppb).

34. The system of any of the clauses herein, wherein the measured concentration of nitrite in the liquid solution of the bioreactor is between 50 and 400 parts per billion (ppb).

35. The system of any one of the clauses herein, wherein the measured concentration of phosphate in the liquid solution of the bioreactor is at least 0.1, 0.3, 0.5, 0.7, or 1.0 parts per million (ppm).

36. The system of any one of the clauses herein, wherein the measured concentration of phosphate in the liquid solution of the bioreactor is at least 0.3 parts per million (ppm).

37. The system of any one of the clauses herein, wherein the measured concentration of phosphate in the liquid solution of the bioreactor is between 0.1 and 1.0 parts per million (ppm).

38. The system of any one of the clauses herein, further comprising a return line positioned to direct a first portion of the sludge from the filter to the bioreactor as return sludge, wherein: the controller is configured to regulate a return rate of the return sludge based on a sludge retention time of at least 15 days, 20 days, 30 days, 60 days, or 120 days, and the sludge retention time equals a volume of the liquid solution divided by a remaining portion of the sludge that is not return sludge, wherein the sludge retention time is based on a thickening of the sludge by the filter.

39. The system of any one of the clauses herein, further comprising a return line positioned to direct a first portion of the sludge from the filter to the bioreactor as return sludge, wherein:
the controller is configured to regulate a return rate of the return sludge based on a sludge retention time of at least 15 days, and
the sludge retention time equals a volume of the liquid solution divided by a remaining portion of the sludge that is not return sludge, wherein the sludge retention time is based on a thickening of the sludge by the filter.

40. The system of any one of the clauses herein, further comprising a return line positioned to direct a first portion of the sludge from the filter to the bioreactor as return sludge, wherein:
the controller is configured to regulate a return rate of the return sludge based on a sludge retention time between 15 and 120 days, and
the sludge retention time equals a volume of the liquid solution divided by a remaining portion of the sludge that is not return sludge, wherein the sludge retention time is based on a thickening of the sludge by the filter.

41. The system of any one of the clauses herein, further comprising (i) a return line positioned to direct a first portion of the sludge from the filter to the bioreactor as return sludge, and (ii) a waste line positioned to direct a second portion of the sludge from the filter away from the bioreactor as waste sludge, wherein:
the controller is configured to regulate a return rate of the return sludge based on a sludge retention time of at least 15 days, 20 days, 30 days, 60 days, or 120 days,
the sludge retention time equals a volume of the liquid solution divided by a waste rate of the waste sludge, wherein the sludge retention time is based on a thickening of the sludge by the filter.

42. The system of any one of the clauses herein, further comprising (i) a return line positioned to direct a first portion of the sludge from the filter to the bioreactor as return sludge, and (ii) a waste line positioned to direct a second portion of the sludge from the filter away from the bioreactor as waste sludge, wherein:
the controller is configured to regulate a return rate of the return sludge based on a sludge retention time of at least 15 days,
the sludge retention time equals a volume of the liquid solution divided by a waste rate of the waste sludge, wherein the sludge retention time is based on a thickening of the sludge by the filter.

43. The system of any one of the clauses herein, further comprising (i) a return line positioned to direct a first portion of the sludge from the filter to the bioreactor as return sludge, and (ii) a waste line positioned to direct a second portion of the sludge from the filter away from the bioreactor as waste sludge, wherein:
the controller is configured to regulate a return rate of the return sludge based on a sludge retention time between 15 and 120 days,
the sludge retention time equals a volume of the liquid solution divided by a waste rate of the waste sludge, wherein the sludge retention time is based on a thickening of the sludge by the filter.

44. The system of any one of the clauses herein, wherein the liquid solution of the bioreactor has a hydraulic residence time of at most 0.5 days, 1 day, 5 days, 10 days, or 20 days.

45. The system of any one of the clauses herein, wherein the liquid solution of the bioreactor has a hydraulic residence time of at most 20 days.

46. The system of any one of the clauses herein, wherein the liquid solution of the bioreactor has a hydraulic residence time between 0.5 days and 20 days.

47. The system of any one of the clauses herein, further comprising (i) a return line positioned to direct a first portion of the sludge from the filter to the bioreactor as return sludge, and (ii) a waste line positioned to direct a second portion of the sludge from the filter away from the bioreactor as waste sludge, wherein the controller is configured to regulate a return rate of the return sludge and/or a waste rate of the waste sludge based on a measured pH.

48. The system of any one of the clauses herein, further comprising (i) a return line positioned to direct a first portion of the sludge from the filter to the bioreactor as return sludge, and (ii) a waste line positioned to direct a second portion of the sludge from the filter away from the bioreactor as waste sludge, wherein the controller is configured to regulate a return rate of the return sludge and/or a waste rate of the waste sludge based on a mass flow of nitrogen and/or phosphorus of the feed to the bioreactor.

49 The system of any one of the clauses herein, further comprising (i) a return line positioned to direct a first portion of the sludge from the filter to the bioreactor as return sludge, and (ii) a waste line positioned to direct a second portion of the sludge from the filter away from the bioreactor as waste sludge, wherein the controller is configured to regulate a return rate of the return sludge and/or a waste rate of the waste sludge based on a metabolic rate of the AOB.

50. The system of any one of the clauses herein, further comprising (i) a return line positioned to direct a first portion of the sludge from the filter to the bioreactor as return sludge at a first flow rate, and (ii) a waste line positioned to direct a second portion of the sludge from the filter away from the bioreactor as waste sludge at a second flow rate less than the first flow rate.

51. The system of any one of the clauses herein, further comprising:
  a blower positioned to introduce air to the bioreactor; and
  an oxygen sensor positioned to measure oxygen and/or dissolved oxygen in the bioreactor,
  wherein the controller is operably coupled to the blower and the oxygen sensor and is configured to adjust operation of the blower based at least in part on the measured oxygen.

52. The system of any one of the clauses herein, further comprising:
  a return line positioned to direct a portion of the sludge from the filter to the bioreactor as return sludge;
  a heat exchanger positioned to increase and/or decrease a temperature of the return sludge; and
  a temperature sensor positioned to measure a temperature of the liquid solution in the bioreactor,
  wherein the controller is operably coupled to the temperature sensor and the heat exchanger and is configured to adjust operation of the heat exchanger based on the measured temperature.

53. The system of any one of the clauses herein, further comprising:
  a return line positioned to direct a portion of the sludge from the filter to the bioreactor as return sludge;
  a waste line positioned to direct a second portion of the sludge from the filter away from the bioreactor as waste sludge;
  a reverse osmosis unit positioned to (i) receive the permeate and (ii) produce a retentate; and
  an evaporator positioned to (i) receive the retentate and (ii) produce a concentrated product of the ammonium nitrate,
  wherein the controller is configured to regulate a return rate of the return sludge, a waste rate of the waste sludge, and/or a mass flow of nitrogen and/or phosphorus of the feed based on a pH and/or the measured concentration of the liquid solution such that the mass flow of nitrogen and/or phosphorus of the feed corresponds to a metabolic rate of the AOB.

54 The system of any one of the clauses herein, wherein the bioreactor includes organic sodium bicarbonate as an alkalinity source to support complete nitrification of contents of the bioreactor prior to receiving the feed comprising ammonia.

55. The system of any one of the clauses herein, wherein the liquid solution has an alkalinity, defined as a mass of alkalinity as calcium carbonate/a mass of nitrified nitrogen, of at most 0.5, 1, 2, or 3.6.

56. The system of any one of the clauses herein, wherein the liquid solution has an alkalinity, defined as a mass of alkalinity as calcium carbonate/a mass of nitrified nitrogen, of at most 3.6.

57. The system of any one of the clauses herein, wherein the liquid solution has an alkalinity, defined as a mass of alkalinity as calcium carbonate/a mass of nitrified nitrogen, between 0.5 and 3.6.

58. The system of any one of the clauses herein, wherein an amount of the AOB by mass is greater than an amount of the NOB by mass.

59. The system of any one of the clauses herein, wherein an amount of the AOB by mass is less than an amount of the NOB by mass.

60. The system of any one of the clauses herein, wherein a food to microorganism ratio is measured in units of food per mass of biomass per unit time, and wherein the food to microorganism ratio for the AOB is at most 0.5-2.3 (lbs of ammonia oxidized/lbs AOB as chemical oxygen demand (COD))/day.

61. The system of any one of the clauses herein, wherein a food to microorganism ratio is measured in units of food per mass of biomass per unit time, and wherein the food to microorganism ratio for the NOB is at most 0.3-9 (lbs of nitrite oxidized/lbs NOB as chemical oxygen demand (COD))/day.

62. The system of any one of the clauses herein, wherein an amount of the AOB in the liquid solution of the bioreactor is at most 400-3600 mg/L chemical oxygen demand (COD) AOB.

63. The system of any one of the clauses herein, wherein an amount of the NOB in the liquid solution of the bioreactor is at least 100-6000 mg/L chemical oxygen demand (COD) NOB.

64. The system of any one of the clauses herein, wherein an ammonia nitrogen (NH3-N): chemical oxygen demand (COD) AOB/day ratio in the liquid solution of the bioreactor is at most 0.5, 1, 2.5, 4.5, or 5 mg-N/mg-COD AOB/day.

65. The system of any one of the clauses herein, wherein an ammonia nitrogen (NH3-N): chemical oxygen demand (COD) AOB/day ratio in the liquid solution of the bioreactor is at most 5 mg-N/mg-COD AOB/day.

66. The system of any one of the clauses herein, wherein an ammonia nitrogen (NH3-N): chemical oxygen demand (COD) AOB/day ratio in the liquid solution of the bioreactor is between 0.5 and 5 mg-N/mg-COD AOB/day.

67. The system of any one of the clauses herein, wherein a nitrite nitrogen (NO2-N): chemical oxygen demand (COD) NOB/day ratio in the liquid solution of the bioreactor is at most 0.15, 0.6, 1.5, 3, or 9 mg-N/mg-COD NOB/day.

68. The system of any one of the clauses herein, wherein a nitrite nitrogen (NO2-N): chemical oxygen demand (COD) NOB/day ratio in the liquid solution of the bioreactor is at most 9 mg-N/mg-COD NOB/day.

69. The system of any one of the clauses herein, wherein a nitrite nitrogen (NO2-N): chemical oxygen demand (COD) NOB/day ratio in the liquid solution of the bioreactor is between 0.15 and 9 mg-N/mg-COD NOB/day.

70. The system of any one of the clauses herein, wherein a growth rate of the NOB is greater than a growth rate of the AOB until the NOB becomes substrate-limited.

71. The system of any one of the clauses herein, wherein the mixed liquor comprises ammonia and ammonium, and wherein the ammonia and the ammonium are buffers to maintain a pH of the liquid solution.

72. The system of any one of the clauses herein, wherein the mixed liquor comprises the ammonia, ammonium, and nitrates.

73. The system of any one of the clauses herein, wherein the mixed liquor comprises approximately equal parts (i) nitrate nitrogen and (i) ammoniacal nitrogen.

74. The system of any one of the clauses herein, wherein the mixed liquor does not comprise nitrite nitrogen (NO2-N) or comprises at most 0.1, 1, 10, 25, or 50 parts per million (ppm) nitrite nitrogen.

75. The system of any one of the clauses herein, wherein the mixed liquor does not comprise nitrite nitrogen (NO2-N) or comprises at most 50 parts per million (ppm) nitrite nitrogen.

76. The system of any one of the clauses herein, wherein the mixed liquor does not comprise nitrite nitrogen (NO2-N) or comprises between 0.1 and 50 parts per million (ppm) nitrite nitrogen.

77. The system of any one of the clauses herein, wherein the mixed liquor does not comprise nitrite or comprises at most 50, 100, 200, or 400 parts per billion (ppb) nitrite.

78. The system of any one of the clauses herein, wherein the mixed liquor does not comprise nitrite or comprises at most 100 parts per billion (ppb) nitrite.

79. The system of any one of the clauses herein, wherein the mixed liquor does not comprise nitrite nitrogen (NO2-N) or comprises between 50 and 400 parts per billion (ppb) nitrite.

80. The system of any one of the clauses herein, wherein the feed further comprises ammonium and phosphorus.

81. The system of any one of the clauses herein, wherein the feed further comprises unprocessed manure.

82. The system of any one of the clauses herein, wherein phosphorus is a limiting nutrient in the bioreactor, and wherein the feed comprises biochemical oxygen demand (BOD) and a carbon:phosphorus ratio of at most 90:1, 95:1, 100:1, 105:1, 110:1, or 115:1.

83. The system of any one of the clauses herein, wherein phosphorus is a limiting nutrient in the bioreactor, and wherein the feed comprises biochemical oxygen demand (BOD) and a carbon:phosphorus ratio of at most 100:1.

84 The system of any one of the clauses herein, wherein phosphorus is a limiting nutrient in the bioreactor, and wherein the feed comprises biochemical oxygen demand (BOD) and a carbon:phosphorus ratio between 90:1 and 115:1.

85. The system of any one of the clauses herein, wherein the feed comprises no biochemical oxygen demand (BOD) and a carbon:phosphorus ratio of 0:1.

86. The system of any one of the clauses herein, wherein the bioreactor comprises a carbon:nitrogen ratio of at most 1:1, 5:1, 10:1, 15:1, or 20:1.

87. The system of any one of the clauses herein, wherein the bioreactor comprises a carbon:nitrogen ratio of at most 20:1.

88. The system of any one of the clauses herein, wherein the bioreactor comprises a carbon:nitrogen ratio between 1:1 and 20:1.

89. The system of any one of the clauses herein, wherein the bioreactor comprises a carbon:nitrogen ratio of 0.

90. The system of any one of the clauses herein, wherein phosphorus is a limiting nutrient in the bioreactor, and wherein the feed comprises biochemical oxygen demand (BOD) and a nitrogen:phosphorus ratio of at least 5:1, 6:1, 7.5:1, 10:1, 15:1, 20:1, or 25:1.

91. The system of any one of the clauses herein, wherein the feed comprises no biochemical oxygen demand (BOD) and a nitrogen:phosphorus ratio of at least 350:1, 375:1, 400:1, 425:1, 450:1, or 475:1.

92. The system of any one of the clauses herein, wherein the feed comprises biochemical oxygen demand (BOD) and a carbon:nitrogen:phosphorus ratio of at most 10:310:1, 15:335:1, 20:360:1, 25:385:1, 30:410:1, or 35:435:1.

93. The system of any one of the clauses herein, wherein the permeate does not include the AOB or the NOB.

94. The system of any one of the clauses herein, wherein the permeate is configured to be used in organic crop production under U.S. Department of Agriculture National Organic Program.

95. A method for producing ammonium nitrate via a bioreactor, the method comprising: receiving, at the bioreactor, a feed comprising ammonia;
   producing a mixed liquor via the bioreactor, wherein the bioreactor holds a liquid solution having (i) an ammonia oxidizing bacteria (AOB) configured to facilitate oxidation of the ammonia to produce a nitrite, and (ii) a nitrite oxidizing bacteria (NOB) configured to facilitate oxidation of the nitrite;
   filtering the mixed liquor to produce a permeate and a sludge; and
   controlling a concentration of the liquid solution to cause (i) partial oxidation of the ammonia in the liquid solution and (ii) complete oxidation of the nitrite in the liquid solution.

96. The method of any one of the clauses herein, further comprising:
   controlling a mass flow of nitrogen and/or phosphorus of the feed to be mixed with the liquid solution held by the bioreactor, wherein the feed comprises the ammonia, and wherein the liquid solution comprises the AOB and the NOB;
   obtaining a return rate of a return sludge to be mixed with the liquid solution;
   obtaining the concentration of the liquid solution; and
   adjusting the mass flow of nitrogen and/or phosphorus of the feed based at least in part on the obtained concentration of the liquid solution.

97. The method of any one of the clauses herein, further comprising controlling biological activity by regulating a wasting rate of the sludge.

98. The method of any one of the clauses herein, further comprising controlling biological activity by regulating a mass flow of phosphorous of the feed.

99. The method of any one of the clauses herein, further comprising controlling biological activity by regulating a mass flow of phosphorous of the feed utilizing unprocessed manure.

100. The method of any one of the clauses herein, further comprising controlling biological activity by regulating a mass flow of nitrogen of the feed.

101. The method of any one of the clauses herein, further comprising controlling biological activity by regulating a mass flow of nitrogen of the feed corresponds to a metabolic rate of the AOB.

102. The method of any one of the clauses herein, further comprising utilizing a chemical inhibitor, ultraviolet light, and/or a laser to regulate an amount of the AOB and/or the NOB.

103. The method of any one of the clauses herein, further comprising measuring pH of the liquid solution; and regulating a mass flow of nitrogen and/or phosphorus of the feed to the bioreactor based on the measured pH of the liquid solution.

104. The method of any one of the clauses herein, further comprising measuring a phosphate concentration of the liquid solution; and regulating a mass flow of nitrogen and/or phosphorus of the feed to the bioreactor based on a measured nitrite concentration of the liquid solution.

105. The method of any one of the clauses herein, further comprising measuring a phosphorous concentration of the liquid solution; and regulating a mass flow of nitrogen and/or phosphorus of the feed to the bioreactor based on a measured nitrite concentration of the liquid solution.

106. The method of any one of the clauses herein, further comprising measuring an ammonia concentration of the liquid solution; and regulating a mass flow of nitrogen and/or phosphorus of the feed to the bioreactor based on the measured ammonia concentration of the liquid solution.

107. The method of any one of the clauses herein, further comprising measuring an ammonium concentration of the liquid solution; and regulating a mass flow of nitrogen and/or phosphorus of the feed to the bioreactor based on the measured ammonium concentration of the liquid solution.

108. The method of any one of the clauses herein, further comprising measuring a nitrate concentration of the liquid solution; and regulating a mass flow of nitrogen and/or phosphorus of the feed to the bioreactor based on the measured nitrate concentration of the liquid solution.

109. The method of any one of the clauses herein, further comprising controlling biological activity by regulating a mass flow of nitrogen and/or phosphorous of the feed.

110. The method of any one of the clauses herein, further comprising measuring a nitrite concentration of the liquid solution; and regulating a mass flow of nitrogen and/or phosphorus of the feed to the bioreactor based on the measured nitrite concentration of the liquid solution.

111. The method of any one of the clauses herein, further comprising measuring a pH of the liquid solution; and regulating a mass flow of nitrogen and/or phosphorus of the feed to the bioreactor based on the measured pH, by maintaining the pH of the liquid solution at most 6.5, 6.6, 6.7, 6.8, 6.9, or 7.0.

112. The method of any one of the clauses herein, further comprising measuring a pH of the liquid solution; and regulating a mass flow of nitrogen and/or phosphorus of the feed to the bioreactor based on the measured pH, by maintaining the pH of the liquid solution at most 7.0.

113. The method of any one of the clauses herein, further comprising measuring a pH of the liquid solution; and regulating a mass flow of nitrogen and/or phosphorus of the feed to the bioreactor based on the measured pH, by maintaining the pH of the liquid solution between 6.5 and 7.0.

114. The method of any one of the clauses herein, further comprising measuring a pH of the liquid solution; and regulating a mass flow of nitrogen and/or phosphorus of the feed to the bioreactor based on the measured pH, by maintaining the pH of the liquid solution at most 4.0, 4.5, 5.0, 5.5, and 6.0.

115. The method of any one of the clauses herein, further comprising measuring a pH of the liquid solution; and regulating a mass flow of nitrogen of the feed to the bioreactor based on the measured pH, by maintaining the pH of the liquid solution at most 6.0.

116. The method of any one of the clauses herein, further comprising measuring a pH of the liquid solution; and regulating a mass flow of nitrogen and/or phosphorus of the feed to the bioreactor based on the measured pH, by maintaining the pH of the liquid solution between 4.0 and 6.0.

117. The method of any one of the clauses herein, further comprising measuring a pH of the liquid solution; and regulating a mass flow of nitrogen and/or phosphorus of the feed to the bioreactor based on the measured pH to maintain the pH of the liquid solution within a range of 4.0-7.0, 5.6-6.9, 5.7-6.8, 5.8-6.7, 5.9-6.6, or 6.0-6.5.

118. The method of any one of the clauses herein, further comprising measuring a pH of the liquid solution; and regulating a mass flow of nitrogen and/or phosphorus of the feed to the bioreactor based on the measured pH to maintain the pH of the liquid solution within a range of 4.0-7.0.

119. The method of any one of the clauses herein, further comprising regulating a mass flow of nitrogen and/or phosphorus of the feed to the bioreactor based on a measured concentration to (i) inhibit a rate of nitritation relative to a rate of nitratation within the bioreactor, and/or (ii) promote the rate of nitratation relative to the rate of nitritation within the bioreactor.

120. The method of any one of the clauses herein, further comprising regulating a mass flow of nitrogen and/or phosphorus of the feed to the bioreactor based on a measured concentration to promote non-complete nitritation and complete nitratation within the bioreactor.

121. The method of any one of the clauses herein, wherein an ammonia nitrogen (NH3-N): chemical oxygen demand (COD) AOB/day ratio in the liquid solution of the bioreactor is at most 0.5, 1, 2.5, 4.5, or 5 mg-N/mg-COD AOB/day.

122. The method of any one of the clauses herein, wherein an ammonia nitrogen (NH3-N): chemical oxygen demand (COD) AOB/day ratio in the liquid solution of the bioreactor is at most 5 mg-N/mg-COD AOB/day.

123. The method of any one of the clauses herein, wherein an ammonia nitrogen (NH3-N): chemical oxygen demand (COD) AOB/day ratio in the liquid solution of the bioreactor is between 0.5 and 5 mg-N/mg-COD AOB/day.

124. The method of any one of the clauses herein, wherein a nitrite nitrogen (NO2-N): chemical oxygen demand (COD) NOB/day ratio in the liquid solution of the bioreactor is at most 0.15, 0.6, 1.5, 3, or 9 mg-N/mg-COD NOB/day.

125. The method of any one of the clauses herein, wherein a nitrite nitrogen (NO2-N): chemical oxygen demand (COD) NOB/day ratio in the liquid solution of the bioreactor is at most 9 mg-N/mg-COD NOB/day.

126. The method of any one of the clauses herein, wherein a nitrite nitrogen (NO2-N): chemical oxygen demand (COD) NOB/day ratio in the liquid solution of the bioreactor is between 0.15 and 9 mg-N/mg-COD NOB/day.

127. The method of any one of the clauses herein, wherein a measured concentration of phosphate in the liquid solution of the bioreactor is at least 0.1, 0.3, 0.5, 0.7, or 1.0 parts per million (ppm).

128. The method of any one of the clauses herein, wherein a measured concentration of phosphate in the liquid solution of the bioreactor is at least 0.3 parts per million (ppm).

129. The method of any of the clauses herein, wherein a measured concentration of phosphate in the liquid solution of the bioreactor is between 0.1 and 1.0 parts per million (ppm).

130. The method of any of the clauses herein, wherein a measured concentration of nitrite in the liquid solution of the bioreactor is at most 50, 100, 200, or 400 parts per billion (ppb).

131. The method of any of the clauses herein, wherein a measured concentration of nitrite in the liquid solution of the bioreactor is at most 100 parts per billion (ppb).

132. The method of any of the clauses herein, wherein a measured concentration of nitrite in the liquid solution of the bioreactor is between 50 and 400 parts per billion (ppb).

133. The method of any of the clauses herein, wherein the mixed liquor does not comprise nitrite nitrogen (NO2-N) or comprises at most 0.1, 1, 10, 25, or 50 parts per million (ppm) nitrite nitrogen.

134. The method of any of the clauses herein, wherein the mixed liquor does not comprise nitrite nitrogen (NO2-N) or comprises at most 50 parts per million (ppm) nitrite nitrogen.

135. The method of any of the clauses herein, wherein the mixed liquor does not comprise nitrite nitrogen (NO2-N) or comprises between 0.1 and 50 parts per million (ppm) nitrite nitrogen.

136. The method of any of the clauses herein, wherein the mixed liquor does not comprise nitrite or comprises at most 50, 100, 200, or 400 parts per billion (ppb) nitrite.

137. The method of any of the clauses herein, wherein the mixed liquor does not comprise nitrite or comprises at most 100 parts per billion (ppb) nitrite.

138. The method of any of the clauses herein, wherein the mixed liquor does not comprise nitrite nitrogen (NO2-N) or comprises between 50 and 400 parts per billion (ppb) nitrite.

139. The method of any one of the clauses herein, further comprising directing a first portion of the sludge from a filter to the bioreactor as return sludge; and regulating a return rate of the return sludge based on a sludge retention time of at least 15 days, 20 days, 30 days, 60 days, or 120 days.

140. The method of any one of the clauses herein, further comprising directing a first portion of the sludge from a filter to the bioreactor as return sludge; and regulating a return rate of the return sludge based on a sludge retention time of at least 15 days.

141. The method of any one of the clauses herein, further comprising directing a first portion of the sludge from a filter to the bioreactor as return sludge; and regulating a return rate of the return sludge based on a sludge retention time between 15 days and 120 days.

142. The method of any one of the clauses herein, wherein the liquid solution of the bioreactor has a hydraulic residence time of at most 0.5 days, 1 day, 5 days, 10 days, or 20 days.

143. The method of any one of the clauses herein, wherein the liquid solution of the bioreactor has a hydraulic residence time of at most 20 days.

144. The method of any one of the clauses herein, wherein the liquid solution of the bioreactor has a hydraulic residence time between 0.5 days and 20 days.

145. The method of any one of the clauses herein, further comprising:
directing a first portion of the sludge from a filter to the bioreactor as return sludge;
directing a second portion of the sludge from the filter away from the bioreactor as waste sludge; and
regulating a return rate of the return sludge and/or a waste rate of the waste sludge based on a measured pH.

146. The method of any one of the clauses herein, further comprising:
directing a first portion of the sludge from a filter to the bioreactor as return sludge;
directing a second portion of the sludge from the filter away from the bioreactor as waste sludge; and
regulating a return rate of the return sludge and/or a waste rate of the waste sludge based on a mass flow of nitrogen and/or phosphorus of the feed to the bioreactor.

147. The method of any one of the clauses herein, further comprising:
directing a first portion of the sludge from a filter to the bioreactor as return sludge;
directing a second portion of the sludge from the filter away from the bioreactor as waste sludge; and
regulating a return rate of the return sludge and a waste rate of the waste sludge such that a sum of the waste rate of the waste sludge and a flow rate of the permeate is less than a sum of the return rate of the return sludge and a flow rate of the feed.

148. The method of any one of the clauses herein, further comprising:
directing a first portion of the sludge from a filter to the bioreactor as return sludge;
directing a second portion of the sludge from the filter away from the bioreactor as waste sludge; and
regulating a return rate of the return sludge and a waste rate of the waste sludge such that the waste rate of the waste sludge is less than the return rate of the return sludge.

149. The method of any one of the clauses herein, further comprising:
introducing air to the bioreactor via a blower;
measuring oxygen and/or dissolved oxygen in the bioreactor via an oxygen sensor; and
adjusting operation of the blower based on the measured oxygen.

150. The method of any one of the clauses herein, further comprising:
directing a portion of the sludge from a filter to the bioreactor as return sludge;
adjusting a temperature of the return sludge via a heat exchanger;
measuring a temperature of the liquid solution in the bioreactor via a temperature sensor; and
adjusting operation of the heat exchanger based on the measured temperature.

151. The method of any one of the clauses herein, further comprising:
directing a first portion of the sludge from a filter to the bioreactor as return sludge;
directing a second portion of the sludge from the filter away from the bioreactor as waste sludge;
directing the permeate through a semi-permeable membrane such that water molecules of the permeate pass through the semi-permeable membrane to produce a retentate comprising the remaining molecules of the permeate;

evaporating water molecules of the retentate to produce a concentrated product of the ammonium nitrate; and regulating a return rate of the return sludge, a waste rate of the waste sludge, and/or a mass flow of nitrogen and/or phosphorus of the feed based on a pH and/or a measured concentration of the liquid solution such that the mass flow of nitrogen and/or phosphorus of the feed corresponds to a metabolic rate of the AOB.

152. The method of any one of the clauses herein, further comprising introducing organic sodium bicarbonate into the bioreactor, wherein the organic sodium bicarbonate supports complete nitrification of contents in the bioreactor prior to receiving the feed comprising ammonia.

We claim:

1. An industrial system for producing ammonium nitrate using biological activity, the system comprising:
   a bioreactor positioned to receive a feed comprising ammonia, wherein the bioreactor is configured to hold a liquid solution including (i) an ammonia oxidizing bacteria (AOB) configured to facilitate oxidation of the ammonia to produce a nitrite at a nitritation rate, and (ii) a nitrite oxidizing bacteria (NOB) configured to facilitate oxidation of the nitrite at a nitratation rate to produce a mixed liquor comprising a nitrate;
   a filter positioned to (i) receive the mixed liquor and (ii) produce a permeate and a sludge;
   a sensor positioned to measure a concentration of the liquid solution of the bioreactor; and
   a controller operably coupled to the sensor, wherein the controller is configured to control biological activity within the bioreactor based on the measured concentration of the liquid solution to produce ammonium nitrate.

2. The system of claim 1, wherein the controller is configured to control the biological activity by regulating a wasting rate of the sludge.

3. The system of claim 1, wherein the controller is configured to control the biological activity by regulating a mass flow of nitrogen and/or phosphorus of the feed.

4. The system of claim 1, wherein the controller is configured to control the biological activity by regulating a mass flow of nitrogen of the feed corresponds to a metabolic rate of the AOB.

5. The system of claim 1, wherein the sensor is a pH sensor positioned to measure a pH of the liquid solution, and wherein the controller is configured to regulate a mass flow of nitrogen and/or phosphorus of the feed to the bioreactor based on the measured pH of the liquid solution.

6. The system of claim 1, wherein the sensor is a phosphate sensor positioned to measure a phosphate concentration of the liquid solution, and wherein the controller is configured to regulate a mass flow of nitrogen and/or phosphorus of the feed to the bioreactor based on the measured phosphate concentration of the liquid solution.

7. The system of claim 1, wherein the sensor is a nitrite sensor positioned to measure a nitrite concentration of the liquid solution, and wherein the controller is configured to regulate a mass flow of nitrogen and/or phosphorus of the feed to the bioreactor based on the measured nitrite concentration of the liquid solution.

8. The system of claim 1, wherein the sensor is a pH sensor positioned to measure a pH of the liquid solution, and wherein the controller is configured to regulate a mass flow of nitrogen and/or phosphorus of the feed to the bioreactor based on the measured pH by maintaining the pH of the liquid solution within a range of 4.0-7.0.

9. The system of claim 1, further comprising a return line positioned to direct a first portion of the sludge from the filter to the bioreactor as return sludge, wherein:
   the controller is configured to regulate a return rate of the return sludge based on a sludge retention time of at least 15 days, and
   the sludge retention time equals a volume of the liquid solution divided by a remaining portion of the sludge that is not return sludge, wherein the sludge retention time is based on a thickening of the sludge by the filter.

10. The system of claim 1, wherein the liquid solution of the bioreactor has a hydraulic residence time of at most 20 days.

11. The system of claim 1, further comprising (i) a return line positioned to direct a first portion of the sludge from the filter to the bioreactor as return sludge, and (ii) a waste line positioned to direct a second portion of the sludge from the filter away from the bioreactor as waste sludge, wherein the controller is configured to regulate a return rate of the return sludge and/or a waste rate of the waste sludge based on a measured pH.

12. The system of claim 1, further comprising:
   a blower positioned to introduce air to the bioreactor; and
   an oxygen sensor positioned to measure oxygen and/or dissolved oxygen in the bioreactor,
   wherein the controller is operably coupled to the blower and the oxygen sensor, and is configured to adjust operation of the blower based at least in part on the measured oxygen.

13. The system of claim 1, further comprising:
   a return line positioned to direct a portion of the sludge from the filter to the bioreactor as return sludge;
   a heat exchanger positioned to increase and/or decrease a temperature of the return sludge; and
   a temperature sensor positioned to measure a temperature of the liquid solution in the bioreactor,
   wherein the controller is operably coupled to the temperature sensor and the heat exchanger, and is configured to adjust operation of the heat exchanger based on the measured temperature.

14. The system of claim 1, further comprising:
   a return line positioned to direct a portion of the sludge from the filter to the bioreactor as return sludge;
   a waste line positioned to direct a second portion of the sludge from the filter away from the bioreactor as waste sludge;
   a reverse osmosis unit positioned to (i) receive the permeate and (ii) produce a retentate; and
   an evaporator positioned to (i) receive the retentate and (ii) produce a concentrated product of the ammonium nitrate,
   wherein the controller is configured to regulate a return rate of the return sludge, a waste rate of the waste sludge, and/or a mass flow of nitrogen and/or phosphorus of the feed based on a pH and/or the measured concentration of the liquid solution such that the mass flow of nitrogen and/or phosphorus of the feed corresponds to a metabolic rate of the AOB.

15. A method for producing ammonium nitrate via a bioreactor, the method comprising:
   receiving, at the bioreactor, a feed comprising ammonia;
   producing a mixed liquor via the bioreactor, wherein the bioreactor holds a liquid solution having (i) an ammonia oxidizing bacteria (AOB) configured to facilitate oxidation of the ammonia to produce a nitrite, and (ii) a nitrite oxidizing bacteria (NOB) configured to facilitate oxidation of the nitrite;

filtering the mixed liquor to produce a permeate and a sludge; and controlling a concentration of the liquid solution to cause (i) partial oxidation of the ammonia in the liquid solution and (ii) complete oxidation of the nitrite in the liquid solution.

16. The method of claim 15, further comprising:

controlling a mass flow of nitrogen and/or phosphorus of the feed to be mixed with the liquid solution held by the bioreactor, wherein the feed comprises the ammonia, and wherein the liquid solution comprises the AOB and the NOB;

obtaining a return rate of a return sludge to be mixed with the liquid solution;

obtaining the concentration of the liquid solution; and adjusting the mass flow of nitrogen and/or phosphorus of the feed based at least in part on the obtained concentration of the liquid solution.

17. The method of claim 15, further comprising controlling biological activity by regulating a wasting rate of the sludge.

18. The method of claim 15, further comprising controlling biological activity by regulating a mass flow of nitrogen and/or phosphorous of the feed.

19. The method of claim 15, further comprising controlling biological activity by regulating a mass flow of nitrogen of the feed corresponds to a metabolic rate of the AOB.

20. The method of claim 15, further comprising measuring a pH of the liquid solution; and regulating a mass flow of nitrogen and/or phosphorus of the feed to the bioreactor based on the measured pH to maintain the pH of the liquid solution within a range of 4.0-7.0.

21. The method of claim 15, further comprising directing a first portion of the sludge from a filter to the bioreactor as return sludge; and regulating a return rate of the return sludge based on a sludge retention time of at least 15 days.

22. The method of claim 15, further comprising:

directing a first portion of the sludge from a filter to the bioreactor as return sludge;

directing a second portion of the sludge from the filter away from the bioreactor as waste sludge; and regulating a return rate of the return sludge and a waste rate of the waste sludge such that a sum of the waste rate of the waste sludge and a flow rate of the permeate is less than a sum of the return rate of the return sludge and a flow rate of the feed.

23. The method of claim 15, wherein the liquid solution of the bioreactor has a hydraulic residence time of at most 20 days.

24. The method of claim 15, wherein an ammonia nitrogen (NH3-N): chemical oxygen demand (COD) AOB/day ratio in the liquid solution of the bioreactor is at most 5 mg-N/mg-COD AOB/day.

25. The method of claim 15, wherein a nitrite nitrogen (NO2-N): chemical oxygen demand (COD) NOB/day ratio in the liquid solution of the bioreactor is at most 9 mg-N/mg-COD NOB/day.

26. The method of claim 15, wherein a measured concentration of the nitrite in the liquid solution of the bioreactor is at most 100 parts per billion (ppb).

27. The method of claim 15, wherein a measured concentration of phosphate in the liquid solution of the bioreactor is at least 0.3 parts per million (ppm).

28. The method of claim 15, further comprising:

introducing air to the bioreactor via a blower;

measuring oxygen and/or dissolved oxygen in the bioreactor via an oxygen sensor; and adjusting operation of the blower based at least in part on the measured oxygen.

29. The method of claim 15, further comprising:

directing a portion of the sludge from a filter to the bioreactor as return sludge;

adjusting a temperature of the return sludge via a heat exchanger;

measuring a temperature of the liquid solution in the bioreactor via a temperature sensor; and adjusting operation of the heat exchanger based on the measured temperature.

30. The method of claim 15, further comprising introducing organic sodium bicarbonate into the bioreactor, wherein the organic sodium bicarbonate supports complete nitrification of contents in the bioreactor prior to receiving the feed comprising ammonia.

* * * * *

UNITED STATES PATENT AND TRADEMARK OFFICE
CERTIFICATE OF CORRECTION

| | | |
|---|---|---|
| PATENT NO. | : 12,365,864 B1 | Page 1 of 1 |
| APPLICATION NO. | : 19/025921 | |
| DATED | : July 22, 2025 | |
| INVENTOR(S) | : Stanley Janicki et al. | |

It is certified that error appears in the above-identified patent and that said Letters Patent is hereby corrected as shown below:

In the Drawings

On sheet 2 of 4, in FIG. 2, reference numeral 202, Line 5, delete "nitritE" and insert -- nitrite --.

Signed and Sealed this
Eleventh Day of November, 2025

John A. Squires
*Director of the United States Patent and Trademark Office*